United States Patent
Burbaum et al.

[11] Patent Number: 5,981,207
[45] Date of Patent: Nov. 9, 1999

[54] CAGED ENZYME SUBSTRATES AS PROBES FOR REPORTER ENZYME ACTIVITY

[75] Inventors: Jonathan J. Burbaum, Cranbury; Ke Yang, West Windsor, both of N.J.

[73] Assignee: Pharmacopeia, Inc., Princeton, N.J.

[21] Appl. No.: 09/216,445

[22] Filed: Dec. 18, 1998

[51] Int. Cl.[6] ............................. C12Q 1/42; C12Q 1/00
[52] U.S. Cl. ................................. 435/21; 435/4; 435/968
[58] Field of Search ........................... 435/21, 4, 968

[56] References Cited

U.S. PATENT DOCUMENTS 5,538,847  7/1996  Bronstein et al. ................. 435/21

OTHER PUBLICATIONS

"Handbook of Fluorescent Probes and Research Chemicals", 6th ed., Molecular Probes, Chapter 19, 448–453 (1996).

"Naphthyl Dioxetane Phosphates: Synthesis of Novel Substrates for Enzymatic Chemiluminescent Assays" J. Org. Chem. 1990, 55, 6225–6229.

"Membrane–permeable Luciferin Esters for Assay of Firefly Luciferase in Live Intact Cells" BioChem J. (1991) 276, 637–641.

Düring, K., J. Chrom, 618, 105–131 (1993), Month not available.

Bronstein, L., J. Biolum, Chemilum. 4, 99–111 (1989). Method not available.

Primary Examiner—Louise N. Leary

[57] ABSTRACT

Caged enzyme substrates as probes for detecting reporter enzyme activity in cell-based assays are disclosed. Caged substrates for reporter gene assays are shown as compounds of Formula I or Formula II:

$$(K-G)_m - Z - (G-K)_n \qquad \text{I}$$

$$\begin{array}{c} K_m \diagdown \diagup K_n \\ Z \\ \diagup \diagdown \\ G_m \qquad G_n \end{array} \qquad \text{II}$$

wherein Z is a luminescent functionality; G is a labile group, cleavable by enzymatic action; and K is a photolytically cleavable caging group; wherein m and n are independently 0 or 1, but m and n both can not be zero. Test kits for determining reporter enzyme activity using compounds of Formula I or Formula II and photolytic cleavage to produce a compound of Formula III:

$$G_m - Z - G_n \qquad \text{III}$$

are described. Methods for determining reporter enzyme activity and, by inference, the activator or suppressor activity of a test compound in a cell-based assay are also described.

19 Claims, 1 Drawing Sheet

CAGED ENZYME SUBSTRATES AS PROBES FOR REPORTER ENZYME ACTIVITY

INCORPORATION BY REFERENCE

High Throughput Assay, pending U.S. patent application Ser. No. 08/868,020 filed Jun. 3, 1997, is incorporated herein by reference.

All patents and other literature references cited herein are incorporated by reference.

FIELD OF THE INVENTION

The present invention relates generally to caged enzyme substrates as probes for detecting reporter enzyme activity in cell-based assays. In particular, this invention relates to advantageous methods using such caged enzyme substrates for rapidly detecting and assessing the ability of substances to activate or suppress specific cellular pathways.

BACKGROUND OF THE INVENTION

To identify lead candidates for drug discovery programs, large numbers of compounds are often screened for their activities as enzyme inhibitors or receptor agonists or antagonists. Increased numbers of compounds as part of combinatorial libraries can be screened using microwell plates that allow miniaturization of assays. High throughput screening (HTS) has provided the ability to screen potential drug candidates rapidly on a miniaturized scale as described in pending U.S. patent application Ser. No. 08/868,280, filed Jun. 3, 1997. HTS involving miniaturized microwell plates (1 μL/well) requires both accurate sample handling and sensitive assay methods as described in international patent application Ser. No. PCT/US98/00494, filed Jan. 8, 1998. Typical assay methods involving biological systems and reporter genes require growth conditions for cells that promote reporter gene expression (usually as a reporter enzyme), which can involve specific media and/or an inducer. A further requirement is addition of a necessary substrate for the reporter enzyme, in order to detect a measurable response related to enzyme activity in the presence or absence of an activator or suppressor of the applicable cellular pathway. Currently, each measurement requires a subsequent addition of substrate. Repeated or serial additions increase both the chances for mistakes and the propagated error, and preclude replicate measurements when 'irreversible steps' (e.g., cell lysis) are needed. These multistep methods for HTS represent a disadvantage in achieving a streamlined, efficient assay for evaluating potential drug candidates.

New targets for therapeutic discovery are emerging from current research in human genetics and eukaryotic molecular biology, which enable the identification and understanding of factors that control the level of gene expression at transcriptional and post-transcriptional levels. Humans and other eukaryotic organisms have developed control mechanisms for biological pathways that achieve rapid and concerted responses to environmental stimuli. Often, these control mechanisms exert their influence at the genetic level, by controlling the expression levels of particular genes. The use of reporter genes constitutes an approach to quantitative determination of gene expression. Reporter genes are often coupled to a promoter, enhancer, or other sequence of interest; i.e. two genetic elements including a specifically measurable coding region are fused together as an artificial construct, which is then introduced into the eukaryotic cells. By measuring the level of reporter gene expression from this construct, indirect determination of the effect of the various experimental conditions, including activation or suppression of a receptor, is then possible. By inference, compounds that influence the level of reporter gene expression affect the control mechanisms in whole animal models and human clinical candidates and, therefore, have therapeutic potential.

Conventional reporter genes include those expressing *E. coli* β-galactosidase [β-gal] (An, G., Hidaka, K., Siminovitch, L., *Mol. Cell. Biol.* 2, 1628–1632 (1982)), xanthine-guanine phosphoribosyl transferase (Chu, G., Berg, P., *Nucleic Acid Res.* 13, 2921–2930 (1985)), galactokinase (Schumperli, D., Howard, B., Rosenberg, M., *Proc. Natl. Acad. Sci. USA* 79, 257–261 (1982)), secreted β-lactamase (Cartwright, C. P., Li, Y., Zhu, Y. S., Kang, Y. S., Tipper, D. J., *Yeast* 10, 497–508 (1994)), β-tactamase expressed intracellularly (Zlokarnik, G., Negulescu, P. A., Knapp, T. E., Mere, L., Burres, N., Feng, L., Whitney, M., Roemer, K., and Tsien, R. Y., *Science* 279(5347), 84–88 (1998)), thymidine kinase (Searle, P., Stuart, G., Palmiter, R., *Mol. Cell. Biol.* 5, 1480–1489 (1985)), chloramphenicol acetyltransferase (Gorman, C., Moffat, L., Howard, B., *Mol. Cell. Biol.* 2, 1044–1051 (1982)), secreted alkaline phosphatase (Berger, J., Hauber, J., Hauber, R., Geiger, R., Cullen, B., *Gene* 66, 1–10 (1988); Cullen, B., Malin, M., *Methods Enzymol.* 216, 362–368 (1992); Bronstein, I., *BioTechniques* 17, 172–178, (1994)), urokinase-plasminogen activator (Yokoyama-Kobayashi, M., Sugano, S., Kato, T., Kato, S., *Gene* 163, 193–196 (1995), Zimmerman, M., Quigley, J. P., Ashe, B., Dorn, C., Goldfarb, R., Troll, W., *Proc. Natl. Acad. Sci. USA* 75, 750–753 (1978), Huseby, R. M., et al., *Thrombosis Research* 10, 679 (1977)) and luciferase, which naturally produces a chemiluminescence signal via oxidation of organic molecules such as firefly luciferin (Structure A) (Ow, D. W., Wood, K. V., DeLuca, M.; DeWet, J. R., Helenski, D. R., Howell, S. H., *Science* 234, 856–859, (1986); Ow, D. W., Jacobs, J. D., Howell, S. H., *Proc. Natl. Acad. Sci. USA* 84, 4870–4874, (1987)).

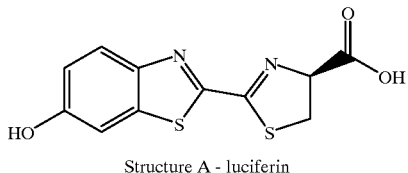

Structure A - luciferin

From among the foregoing list of reporter genes, the gene expressing alkaline phosphatase is a particularly attractive reporter gene, in that its expression can be assayed by a simple, quick calorimetric assay for the product protein. A secreted form of human placental alkaline phosphatase, SEAP, has been readily and accurately quantified within the media of transfected cultures using either a standard calorimetric assay or a bioluminescence-based alkaline phosphatase assay. The SEAP assay has the additional advantage that multiple quantitative assays can be obtained from a single cell culture. The ability to measure levels of secretable alkaline phosphatase from cultured mammalian cells provides a universal method for the indirect determination of factors that influence gene expression (EP 327,960, Aug. 16, 1989). Measurement of SEAP in the presence of an activator or suppressor and under control conditions enables identification of potential drug candidates by their effect on cellular functions. However, SEAP suffers the disadvantage of requiring multiple step additions of substrate to each well at a controlled time to measure the activity of the enzyme within a certain time period.

The gene expressing chloramphenicol acetyltransferase [CAT] is another example of a reporter gene. It has the advantages of high protein stability, high sensitivity, and the absence of interfering activities in eukaryotic cells. Disadvantages of a CAT assay include the necessary harvesting, cell lysis, and extraction of cell cultures prior to a time-consuming assay using an expensive radioactive substrate. Assays based upon SEAP and CAT reporter genes afford results that are qualitatively and quantitatively comparable.

Reporter gene assays are typically used to evaluate agonist (stimulatory) or antagonist (inhibitory) activity of a test compound. For agonist assays, cells that conditionally express the reporter enzyme in the presence of a stimulatory signal are probed. For example, activation or stimulation of the vasoactive intestinal peptide (VIP) receptor in the human embryonic kidney cell line HEK293 is performed by assembling an artificial reporter gene construct wherein the expression of luciferase is induced by the elevation of the cyclic AMP (cAMP) levels by virtue of a genetic response element (CRE) positioned at the 5'-end of the gene. Among its many known intracellular targets, cAMP is known to activate the expression of genes that contain cAMP response elements (CRE) in their promoter/enhancer regions. Stimulation of the VIP receptor is known to cause elevation of the cAMP levels, and consequently, the HEK293(CRE-luc) cell line thus constructed responds to VIP or VIP receptor agonists by increasing the level of luciferase expression. The level of luciferase expression is determined using well-established methods (e.g., LucLite kit, available from Promega, Madison, Wis.).

The human embryonic kidney cell line HEK293 cell line can then be used to screen for VIP agonists as follows: 1) The HEK293(CRE-luc) cell line is grown in a tissue culture dish, such as a 96-well microtiter plate suitably treated for tissue culture work 2) Once the cells have adhered to the microwell surfaces, test compounds are added and the cells continue to grow for 4 to 48 hours in the presence of cell growth medium. The cell growth medium allows for the production of new proteins, and consequently any stimulation of the VIP receptor or of the endogenous pathway leading to gene expression will result in the increased production of luciferase 3) After this incubation period, the medium is removed and the luciferase assay reagent comprised of luciferin, $Mg^{+2}$, and ATP, along with cell lysis reagents, is added. The activity of luciferase is then detected by the chemiluminescence of the proximal oxyluciferin product of the enzymatic reaction. By quantifying the amount of light produced, the amount of luciferase can be compared from one sample to the next and consequently the amount of stimulation of the VIP receptor pathway can be gauged. VIP agonists will therefore appear as brighter wells on an otherwise dimmer background.

For antagonist assays, the steps are similar except that a common activator (in the instance above, VIP) is initially used to bring all wells of the screening assay to a uniform brightness level in the absence of test compound. Compounds are then tested for their ability to decrease the amount of light produced from the luciferase reaction. These two classes of assay can be summarized in the following scheme:

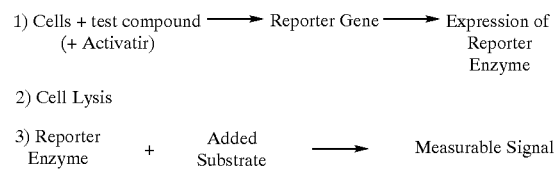

Following the above scheme, cells capable of expressing a reporter enzyme and a test compound are contacted and cells are grown under conditions to encourage expression of a reporter enzyme. In an antagonist assay, a known activator is also added with the cells and test compound to activate the reporter enzyme expression. Cell lysis is required to release the reporter enzyme. Following addition of the enzyme substrate to the media, interaction of the reporter enzyme and the added substrate occurs to produce a signal proportional to the expression of the reporter enzyme in the presence of a test compound. Note that the addition of substrate is done by adding another solution to the cells. This fluid addition step is a disadvantage for cell-based assays because addition of more solution can perturb the cells and dilute the sample so as to preclude a second measurement.

Chemiluminescent detection of reporter gene expression provides flexibility and sensitivity in assays. Chemiluminescent substrates for alkaline phosphatase, such as spiroadamantane-dioxetane compounds allow highly sensitive nucleic acid analysis techniques (During, K., *J. Chrom.* 618, 105–131(1993)). Disodium 3-(4-methoxyspiro[1,2-dioxetane-3,2'-(5'-chloro)tricyclo[$3.3.1.1^{3,7}$]decan]-4-yl) phenyl phosphate (CSPD) and disodium 3-(4-methoxyspiro [1,2-dioxetane-3,2'-tricyclo[$3.3.1.1^{3,7}$]decan]-4-yl)phenyl phosphate (AMPPD) are adamantyl 1,2-dioxetane systems that provide important features for chemiluminescent substrates for alkaline phosphatase or alkaline phosphatase conjugates (Bronstein, I., *J. Biolum. Cherilum.* 4, 99–111 (1989)). In these compounds, the energy source for chemiluminescence is the dioxetane ring; chemical stability of the substrate is provided both by the adamantyl functionality and the phosphate group. The light emission capabilities of the enzyme substrate are defined by the aryl functionality. The activation site for the substrate consists of an enzyme cleavable group, in this case the phosphate ester bond. In general, the enzyme cleavable group imparts a high stability to the system, such that luminescence occurs only when the cleavable group has been removed. In this example, the arylphosphate is dephosphorylated to afford an aryloxide anion. The 1,2-dioxetane aryloxide anion, having a "weak" oxygen-oxygen bond, decomposes to form carbonyl products, and the decomposition releases approximately 400 kJ/mol of energy, resulting in a strong chemiluminescent signal.

For automated assays, a short half-life ($t_{1/2}$) of the dioxetane and a short time required to reach maximum light emission for the reporter molecule are both desirable characteristics. Because the signal from a previous assay must dissipate before a second measurement can be taken, a long half-life lengthens the window between measurements, thus increasing the total time for assay and decreasing efficiency. A longer time for reaching maximum light signal emission also increases overall assay time and decreases reliability of signal readings. Long half-life and an increased time to reach maximum signal emission are disadvantages in high throughput screening assays. Chemiluminescent dioxetane derivatives that have reduced half-lives are described in U.S. Pat. No. 5,538,847, issued Jul. 23, 1996.

Typically, the more popular forms of 1,2-dioxetanes, AMPPD and CSPD (shown below) are incubated with alkaline phosphatase for determined periods of time.

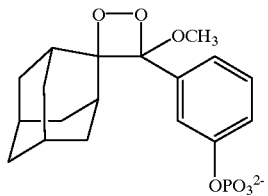

AMPPD

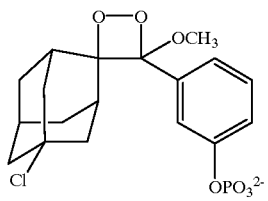

CSPD

CSPD usually achieves maximum light emission at a faster rate than AMPPD when used on nylon membranes in Western blot analysis. (Albrecht, S., et al, "Bioluminescence and Chemiluminescence: Current Status", Stanley, P., Kricka, L.(Eds.), 115–118, (1991)). Reaction of AMPPD with alkaline phosphatase is outlined in Scheme 1.

Scheme 1. Use of Representative SEAP substrate (AMPPD) in measuring SEAP activity in vivo.

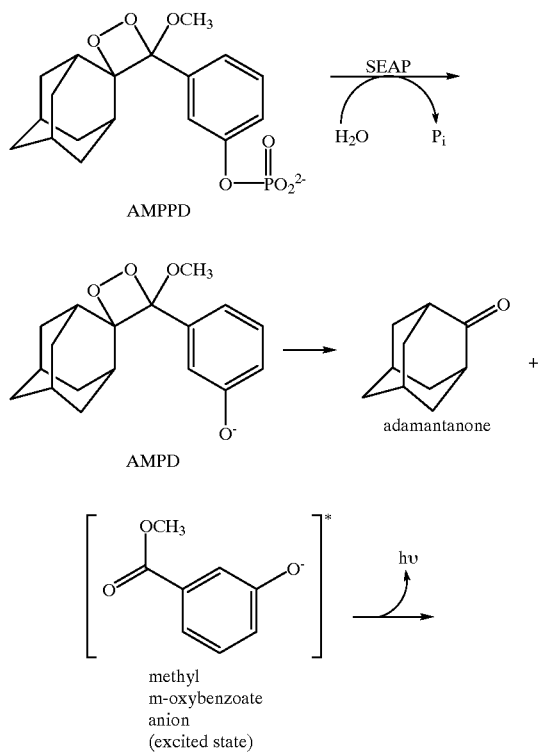

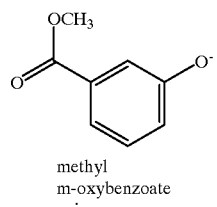

methyl
m-oxybenzoate
anion

Dephosphorylation of the arylphosphate results in a moderately stable anion (AMPD) which decomposes to an adamantanone and methyl m-oxybenzoate, (as a charge-transfer excited species). The excited state of methyl m-oxybenzoate anion emits light at a wavelength of approximately 477 nm. Decomposition of methyl m-oxybenzoate anion results in production of chemiluminescent signal emitted in the form of a glow, with breakdown of the intermediate anion determined by the environment (e.g., the membrane used for blot assay). Exposure time must be optimized for each general assay system to obtain appropriate signals. Generally, CSPD is preferred over AMPPD when longer emission times are needed for assays.

Chemiluminescent detection of SEAP is known. Optimum levels of SEAP in the culture medium usually are obtained 12–24 h after transfection. The levels of SEAP activity detected in the culture medium are directly proportional to changes in intracellular concentrations of its SEAP MRNA. Because the preparation of cell lysates is not necessary to assay for the reporter enzyme and the transfected cell cultures remain intact, repetitive sampling of the culture medium is possible. The assay is adaptable to automation using cultures grown in 96-microwell plates. Endogenous alkaline phosphatase activity can be eliminated by heating the culture to 65° C., and the heat-stability of SEAP allows measurement of expressed SEAP only. Detection of SEAP activity from reporter gene expression requires several fluid manipulation steps involving removal of samples, dilution with buffer, heating and incubation. Addition of the chemiluminescent substrate CSPD and enhancer, followed by incubation, produces a stable chemiluminescent signal in approximately 10 minutes, and the signal remains constant for approximately one hour. However, multiple fluid manipulations, involving serial additions of the chemiluminescent substrate and the enhancer, increase the likelihood of error in measurement, particularly since maximum signal may occur before fluid addition is completed. In such a case, the maximum signal will not be obtained because the time required for fluid manipulations is too long.

A typical assay using secreted placental alkaline phosphatase (SEAP) would be designed by first assembling an artificial reporter gene construct wherein the expression of SEAP reporter gene is induced by the elevation of the cyclic AMP (cAMP) levels by virtue of a genetic response element (CRE), and then measuring the concentration of SEAP released into the medium. The HEK293(CRE-SEAP) cell line thus constructed again responds to VIP or VIP receptor agonists by increasing the level of SEAP expression. Theoretically, the reporter activity could be measured repetitively, since the cells are not destroyed by the measurement of the luminescent signal. However, repeated fluid addition to the same well is not advantageous for screening because multiple fluid additions: (a) increase error levels due to propagation of volumetric error into the overall measurement; and (b) can cause small wells to overflow as assay volumes increase with repetitive addition steps.

Chemiluminescent detection of peptidases is similar to chemiluminescent detection of SEAP and has been demonstrated with several available substrates. One commercially available substrate, CBZ-Gly-Gly-L-Arg-7-amino-4-methylcoumarin, available from Enzyme Systems Products, AMC-056, (Dublin, Calif.) can be used for the assay of urokinase-plasminogen activator. Interaction of the peptidase with the enzyme substrate results in the release of the fluorophore which can be detected as a fluorescent signal. An advantage of using a gene expressing a peptidase as a reporter gene is that the substrates are generally biocompatible and soluble under assay conditions. Another advantage arises from the fact that peptidases are usually secreted in their native environment and are stable extracellularly. Again, the disadvantage of using a peptidase as a reporter gene is that addition of the substrate is required prior to each measurement, thus introducing multiple fluid additions.

The unavailability of methods that enable assay of multiple drug candidates on a miniaturized, microvolume scale has hampered the advancement of drug discovery using high throughput screening methods. Rapid, effective means for identification of compounds that interact with eukaryotic systems to alter reporter gene expression would enhance the value of HTS in identifying potential drug candidates. For HTS applications, minimizing the number of fluid handling steps would improve accuracy and allow for facile miniaturization. It would therefore be desirable to have an enzyme substrate in the assay mixture at the initiation of the assay, but in a form that could not function as a substrate until that function was needed.

SUMMARY OF THE INVENTION

The solution to the foregoing problems would be an inactivated form of a substrate that could be released into an activated form at an appropriate time. We will refer to this as a "caged" enzyme substrate. The caged enzyme substrate would act as a masked probe for determining reporter enzyme activity. At determined time intervals, the cage would be removed by an external stimulus, such as light. The resulting enzyme substrate would serve as a probe to interact with the reporter enzyme and emit a detectable signal; the signal would reflect reporter enzyme activity and, therefore, reporter gene expression.

In accordance with the present invention, caged enzyme substrates are provided as probes for detecting reporter enzyme activity in cell-based assays. The caged enzyme substrates may be used for rapidly detecting and assessing the ability of substances to act as activators or suppressors for specific cellular pathways that regulate transcription of one or more genes.

In one aspect, the present invention is directed to caged substrates of Formula I for reporter gene assays:

(K—G)$_m$—Z—(G—K)$_n$  I wherein:
Z is a luminescent functionality;
G is a labile group, cleavable by enzymatic action; and
K is a photolytically cleavable caging group;
wherein m or n=0 or 1, but m and n both can not be zero.

In another aspect, the present invention is directed to caged substrates of Formula II for reporter gene assays:

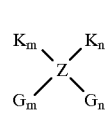

II

Wherein Z, G, K, m and n are as defined above.

The compounds of Formulae I and II perform as caged enzyme substrates to improve the sensitivity, accuracy and speed with which test compounds can be evaluated in cell-based microvolume assays. In the detection system of the invention, the inclusion of the caged substrate in the cell media during all stages of cell growth allows for the temporal monitoring of reporter gene expression.

In yet another aspect, the invention is directed to a test kit for determining reporter enzyme activity and, by inference, the activator or suppressor activity of test compounds in a cell-based assay, preferably using cultured mammalian cells, comprising a compound of Formula I or II:

(K—G)$_m$—Z—(G—K)$_n$  I

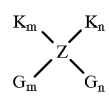

II wherein photolytic cleavage of moieties K produces a compound of Formula III:

G$_m$—Z—G$_n$.  III

In a further aspect, the present invention is directed to a method for determining reporter enzyme activity and, by inference, the activator or suppressor activity of a test compound in a cell-based assay, preferably using cultured mammalian cells, comprising the steps of:

a) adding a compound of Formula I or II:

(K—G)$_m$—Z—(G—K)$_n$  I

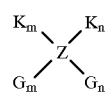

II to a cell sample;
b) contacting said cell sample with a test compound;
c) growing said cell sample such that a reporter gene enzyme is expressed;
d) controlling irradiation of the cell sample containing the compound of Formula I or II to photolytically cleave K and produce a compound of Formula III:

G$_m$—Z—G$_n$;  III e) allowing said reporter gene enzyme to react with said compound of Formula III to enzymatically cleave G and produce a compound, Z, capable of producing a luminescent signal;
f) measuring the luminescent signal; and
g) correlating said signal to the activity of said test compound Interaction of an enzyme substrate, such as a compound of Formula III, with an expressed reporter enzyme results in a compound, Z, which is a luminescent functionality. Energy is emitted from Z to provide a luminescent signal. Chemical bond energy is emitted as a chemiluminescent signal when Z is chemiluminescent. Excitation energy of an incident photon results in a photoluminescent signal when Z is photoluminescent. In this sense, photoluminescent compounds include both fluorescent and phosphorescent compounds.

DETAILED DESCRIPTION OF THE INVENTION

Figure 1:
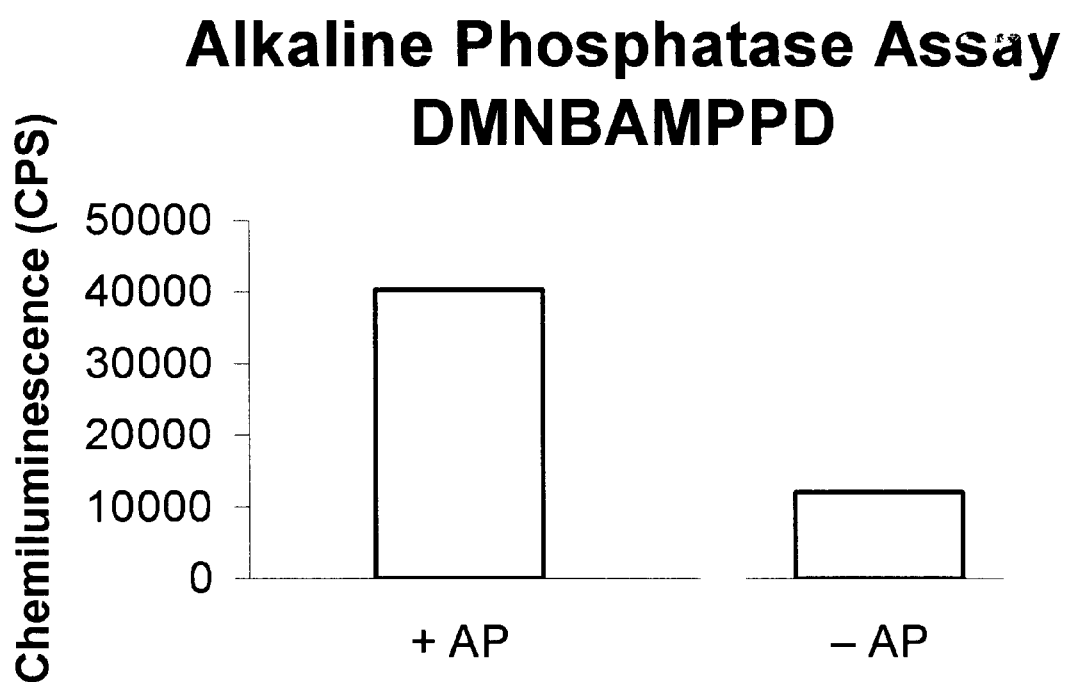
FIG. 1 is a bar graph representation of assay results using DMNBAMPPD as a caged enzyme substrate in a cell-based assay showing chemiluminescence (in counts per second) as a function of the presence or absence of expression of alkaline phosphatase.

For purposes of the discussion herein, certain terms shall be defined as follows:
AMC=aminomethylcoumarin
AMPPD=disodium 3-(4-methoxyspiro[1,2-dioxetane-3,2'-tricyclo[3.3.1.1$^{3,7}$]decan]-4-yl)phenyl phosphate
CBZ=benzyloxycarbonyl
CSPD=disodium 3-(4-methoxyspiro[1,2-dioxetane-3,2'-(5'-chloro)tricyclo[3.3.1.1$^{3,7}$]decan]-4-yl)phenyl phosphate
CCD=charge-coupled device
cps=counts per second
CRE=genetic response element responsive to changes in cyclic AMP levels
DMNAMPPD=4,5-dimethoxy-2-nitrobenzyl caged AMPPD
EBNA1=Epstein Barr virus nuclear antigen 1
ELF=2-(5'-chloro-2'-hydroxyphenyl)-6-chloro-4-(3H)-quinazolinone
Et=ethyl
mL=microliter
HEK=Human Embryonic Kidney
HTS=high throughput screening
min=minutes
NMPPD=disodium 3-(4-methoxyspiro[1,2-dioxetane-3,2'-bicyclo [2.2.1] heptan-4-yl)phenyl phosphate
rt=room temperature, ~22–26° C.
s or sec=seconds
SEAP=secreted alkaline phosphatase
TEA=triethylamine
UV=ultraviolet
VIP=vasoactive intestinal peptide Substituents are defined when introduced and retain that definition throughout this disclosure.

"Alkoxy" means alkoxy groups of from 1 to 20 carbon atoms of a straight, branched, or cyclic configuration and combinations thereof Examples of alkoxy groups include: methoxy, ethoxy, propoxy, isopropoxy, cyclopropyloxy, cyclohexyloxy, and the like.

"Alkyl" is intended to mean linear or branched hydrocarbon structures and combinations thereof. "Lower alkyl" means alkyl groups of from 1 to 20 carbon atoms. Examples of alkyl groups include: methyl, ethyl, propyl, isopropyl, butyl, s-and t-butyl, pentyl, hexyl, octyl, dodecyl, octadecyl, and the like.

"Aryl" is a 6-membered or 10-membered aromatic ring system where each of the rings is optionally substituted with 1–3 substituents selected from alkyl, alkylamino, cyano, halogen, hydroxy, alkoxy, aryloxy, alkoxyethoxy, haloalkyl, phenyl, heteroaryl, nitro, sulfonyl; and wherein the phenyl substituent is optionally substituted with 1–3 substituents selected from alkyl, halogen, nitro or alkoxy. Examples of aryl groups are phenyl, 3,4-dimethoxyphenyl, o-nitrophenyl, naphthyl, and 1-dimethylaminonaphthyl.

"Aralkyl" means an alkyl containing an aryl ring. For example: benzyl, o-nitrobenzyl, phenethyl, 4-chlorobenzyl, naphthylmethylene, and the like.

"Aryloxy" means a phenoxy or naphthyloxy group where the phenyl or naphthyl ring is optionally substituted with 1 to 2 groups selected from halo, alkoxy, or alkyl.

"Cycloalkyl" means cyclic hydrocarbon groups of from 3 to 12 carbon atoms. Examples of "cycloalkyl" groups include: c-propyl, c-butyl, c-pentyl, c-hexyl, 2-methylcyclopropyl, norbornyl, adamantyl, and the like.

"Haloalkyl" means that one or more hydrogen atoms present in an alkyl group are substituted with a halogen atom. For example: trifluoromethyl, 2-chloroethyl, and 2,2, 2-trifluoroethyl.

"Halogen" includes F, Cl, Br, and I, with F and Cl as the preferred groups.

"Heteroaryl" means a 5- or 6-membered heteroaromatic ring containing 0–4 heteroatoms selected from O, N, and S; or a bicyclic 9- or 10- membered heteroaromatic ring system containing 0–4 heteroatoms selected from O, N, and S; where one or more methine H atoms may be optionally substituted with alkyl, alkoxy or halogen. The 5- to 10-membered aromatic heterocyclic rings include: imidazole, pyridine, indole, thiophene, benzopyranone, thiazole, furan, benzimidazole, quinoline, isoquinoline, quinazoline, quinoxaline, pyrimidine, pyrazine, tetrazole, and pyrazole.

"Heteroaralkyl" means an alkyl containing a heteroaryl ring. For example: pyridinylmethyl, pyrimidinylethyl, and the like.

"Heteroatom" means nitrogen, oxygen, or sulfur.

"Substituted alkyl" means an alkyl or branched alkyl optionally substituted with groups such as alkylcarboxylate, alkylcyano, alkylamino, alkyloxy, carboxylate, cyano, haloalkyl, halogen, and nitro.

"Substituted aryl" means an aryl optionally substituted with groups such as alkylcarboxylate, alkylcyano, alkylamino, alkyloxy, carboxylate, cyano, haloalkyl, halogen, and nitro.

"Substituted heteroaryl" means an heteroaryl optionally substituted with groups such as alkylcarboxylate, alkylcyano, alkylamino, alkyloxy, carboxylate, cyano, haloalkyl, halogen, and nitro.

"Substituted aralkyl" means an aralkyl optionally substituted with groups such as alkylcarboxylate, alkylcyano, alkylamino, alkyloxy, carboxylate, cyano, haloalkyl, halogen, and nitro.

"Amino acid" means α-amino acids, β-amino acids, γ-amino acids, and so forth, and all optical isomers thereof Examples of such amino acids include: alanine, asparagine, arginine, cysteine, glutamine, glycine, histidine, isoleucine, leucine, lysine, methionine, phenylalanine, proline, serine, threonine, tryptophan, tyrosine, valine, sarcosine, L-alanine, D-leucine, L-leucine, D-isoleucine, L-isoleucine, D-serine, D-threonine, L-threonine, cis-4-hydroxy-D-proline, cis-4-hydroxy-L-proline, and the like.

"Peptide" means any two or more amino acids linked by an amide bond. Examples of such peptides include: peptides containing proline-arginine, [Pro-Arg] a dipeptide, and leucine-glycine-arginine, [Leu-Gly-Arg] a tripeptide, and the like.

"Peptidase" means an enzyme that cleaves a peptide bond found in shorter peptides. Examples of peptidases include: dipeptidylpeptidase I, II or IV, and the like.

"Protease" means an enzyme that cleaves peptide bonds found in longer peptides and in proteins. Examples of proteases include: serine protease, elastase or prohormone thiol protease, and the like.

"Activator" means a substance capable of positively affecting the production of a particular gene or set of genes, as measured by a reporter gene product in a cell-based assay system.

"Agonist" is a substance that acts at the level of the receptor, generally mimicking the action of a naturally-occurring substance and that activates a cellular response, usually via a signal transduction mechanism.

"Antagonist" is a substance that suppresses or antagonizes the action of an agonist.

"Cage" means a functional group capable of preventing enzymatic cleavage when attached to a labile group. When the cage is removed, the labile group is then susceptible to enzymatic cleavage.

"Combinatorial library" means a collection of molecules based upon a logical design and involving the selective combination of building blocks by means of simultaneous chemical reactions. Each species of molecule in a library is referred to as a member of the library. The combinatorial library represents a collection of molecules of sufficient number and diversity of design to afford a useful molecular population from which to identify biologically active members.

"HEK" means human embryonic kidney cells. "HEK293" is the parental cell line available from the American Type Culture Collection (ATCC, Manassas, Va.).

"High-throughput screening" (HTS) means the process by which a collection of compounds is evaluated, using an efficient assay strategy that correlates with the desired properties of a potentially valuable compound.

"Reporter gene" means a gene that encodes for a protein, the presence of which protein is easily assayed and acts as a signal that can be correlated with the activation or suppression of a cellular pathway of interest.

"Reporter enzyme" means an enzyme expressed by a reporter gene, the presence of which enzyme is easily assayed and acts as a signal that can be correlated with the activation or suppression of a cellular pathway of interest.

"Side-chain-protected amino acid" has the meaning commonly ascribed to it in the peptide art. It refers to an amino acid, such as arginine, lysine, aspartic acid, tyrosine, etc., in which the chemical reactivity of functionality on the amino acid side chain has been masked. Protecting groups for side chains of amino acids are well known, and most such protected amino acids are commercially available. Examples include: aspartic acid β-t-butyl ester, aspartic acid β-benzyl ester, acetamidomethyl cysteine, $N^G$-tosyl arginine, $N^G$-nitro arginine, glutamic acid β-t-butyl ester, glutamic acid β-benzyl ester, $N^{im}$-benzyl histidine, $N^{im}$-tosyl histidine, $N^\epsilon$-tosyl lysine, $N^\epsilon$-CBZ lysine, O-benzyl serine, O-t-butyl serine, O-benzyl tyrosine, O-t-butyl tyrosine, and the like.

"Substrate" means a substance that is acted upon by an enzyme, whereby the enzymatic action modifies the substrate chemically to produce a "product."

"Suppressor" means a substance capable of blocking the action of an activator.

Some of the compounds described herein contain one or more asymmetric centers and may thus give rise to enantiomers, diastereomers, and other stereoisometric forms which may be defined in terms of absolute stereochemistry as (R)- or (S)-, or, for amino acids, as (D) or (L). The present invention is meant to include all such possible diastereomers as well as their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

PREFERRED EMBODIMENTS

As explained above, it would be desirable to have an enzyme substrate that could be introduced into an assay mixture at the initiation of a cell-based assay, but in a form that could not function as an enzyme substrate until that function was needed. This inactivated form we have refered to as a "caged" enzyme substrate. The caged enzyme substrate acts as a masked probe for determining reporter enzyme activity. The concept of caging to provide a means of controlling the release of biologically active products is known. The caging moiety is designed to interfere maximally with the activity of the biologically active product. Typical cages to date have been o-nitrobenzylic compounds that are synthetically incorporated into the target molecule (Greene, T. W.; Wuts, P. G. M. "Protective Groups in Organic Synthesis" $2^{nd}$ ed., 1991). Such cages are detached by photolysis.

The structure of the caging moiety and its bond linkage to the active molecule affect the efficiency of photolytic cleavage and the wavelength required for detachment of the cage. These can be modulated according to known properties (e.g. absorption maxima) of the cage ("Handbook of Fluorescent Probes and Research Chemicals", $6^{th}$ ed., Molecular Probes, Chapter 19, 448–453 (1996)). Other properties such as solubility, stability, uncaging rates, photolysis yields and release of inert byproducts of photolysis are important when considering the choice of caged probes for reporter genes. DMNPE-caged luciferin [1-(4,5-dimethoxy-2-nitrophenyl) ethyl-caged luciferin] is known to be better transported through the cell membrane than is luciferin itself. NPE-caged ATP has been used to measure biological functions, such as contraction of muscle fibers. Photolytic release of ATP produces a biological response (contraction of muscle fibers) which can be measured by physical methods, such as a tensiometer. However, neither of the above examples of a caged probe (DMNPE-caged luciferin or NPE-caged ATP) is useful for measurement of reporter enzyme activity.

A caged substrate for reporter gene assays of the present invention is a compound of I or II:

I

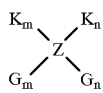

II

In a preferred embodiment of the compounds of Formula I, Z is chosen from the group consisting of 13
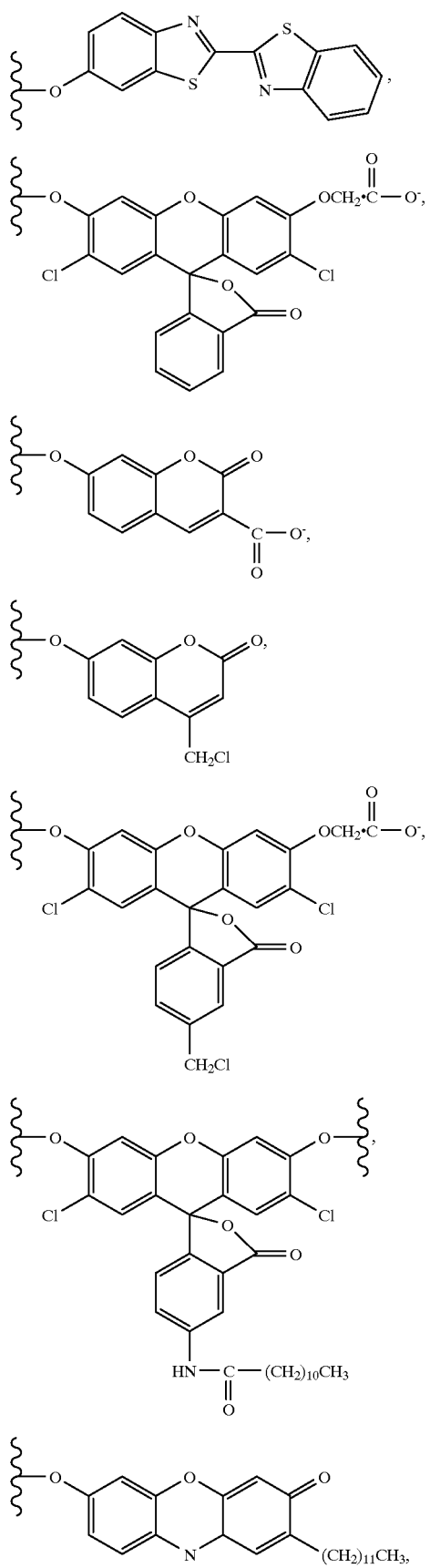
14
-continued
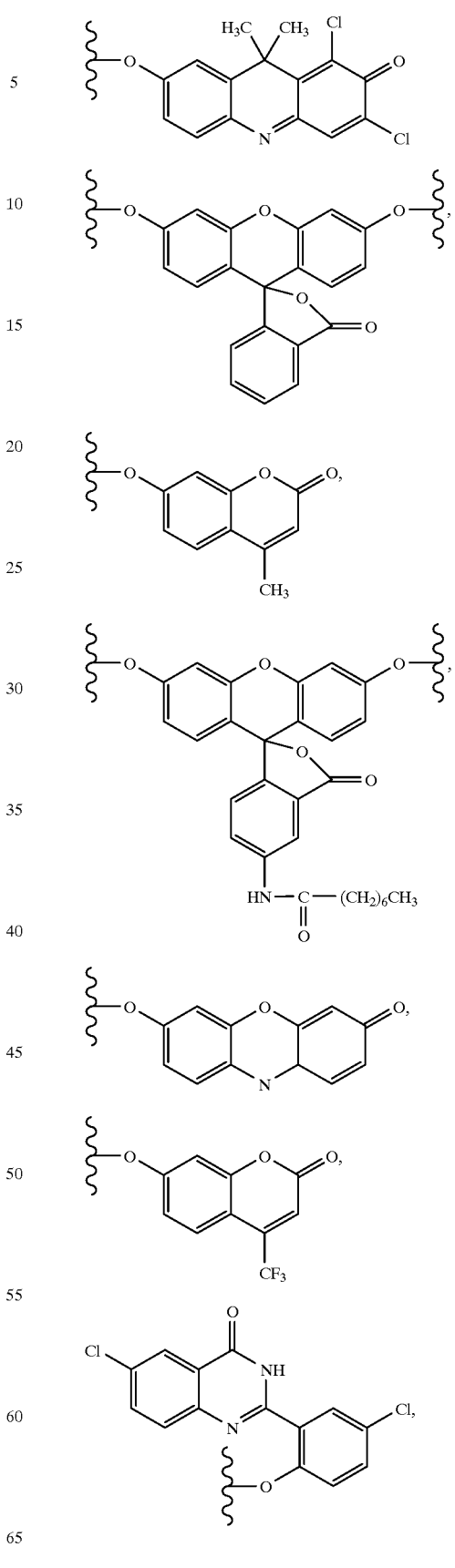

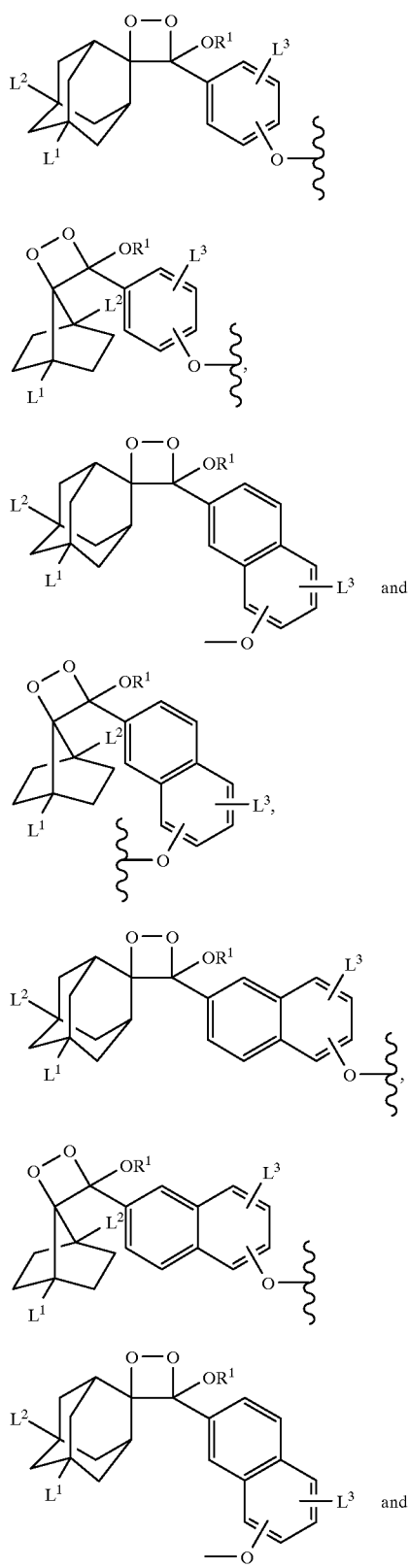

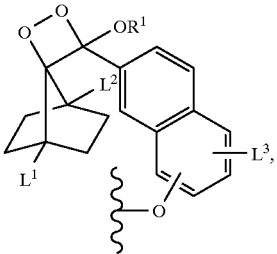

wherein $R^1$ is chosen from the group consisting of $C_{1-12}$ alkyl, substituted alkyl, aryl, substituted aryl, aralkyl and substituted aralkyl;

$L^1$, $L^2$ and $L^3$ are independently alkoxy, alkoxy phenoxy, amide, carboxyl, cyano, halogen, hydrogen, hydroxy, hydroxy alkoxy, phenyl, substituted phenyl or unsubstituted lower alkyl;

G is chosen from the group consisting of phosphate, galactoside, sulfonate, 1-phospho-2,3-diacylglyceride, 1-thio-D-glucoside, adenosine, α-D-glucoside, β-D-glucoside, β-D-glucuronide, β-D-mannoside, β-D-fructofuranoside, and β-glucosiduronate; and K is chosen from the group consisting of substituted benzyl, substituted benzylidene, substituted phenacyl, substituted phenethyl and 1-benzoylbenzyl. Preferred $R^1$ substituents on the 1,2-dioxetanes of the present invention are $C_{1-4}$ alkyl. Preferred $L^1$, $L^2$ and $L^3$ substituents on the 1,2-dioxetanes of the present invention are hydrogen, alkoxy, amide, carboxy and halogen.

Another preferred embodiment of the present invention includes compounds of Formula I wherein:

G is phosphate; and

K is chosen from the group consisting of 2-nitrobenzyl, 1-cyano-1-(2-nitrophenyl)methyl, 4,5-dimethoxy-2-nitrobenzyl, 2-nitrophenethyl, 4,5-dimethoxy-2-nitrophenethyl, phenacyl and substituted phenacyl.

Particularly preferred compounds of the present invention include:

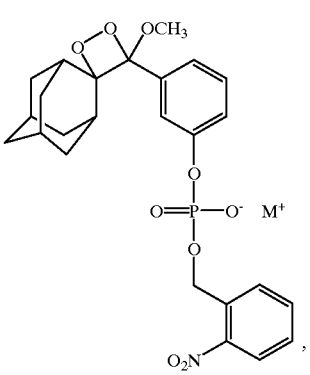

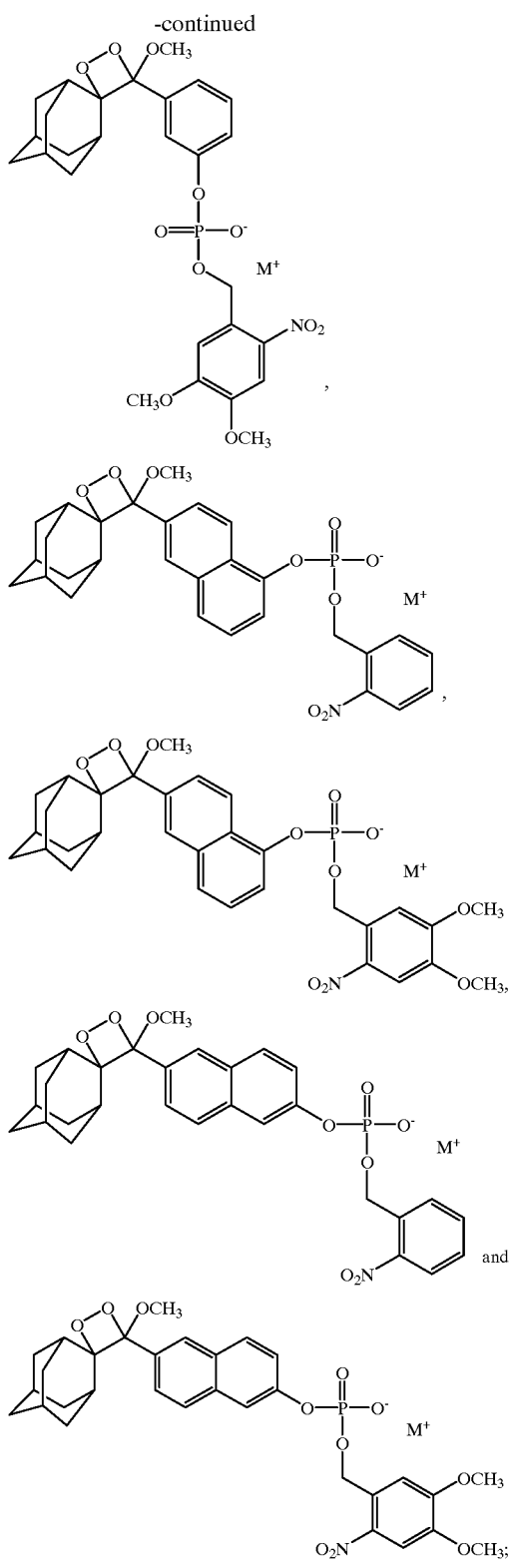

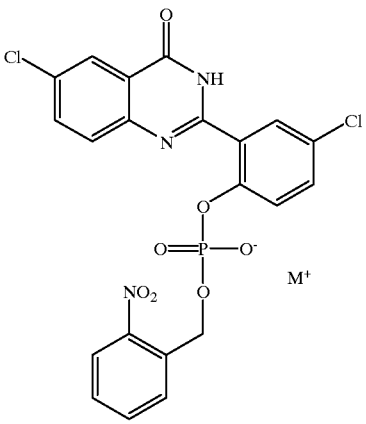

or

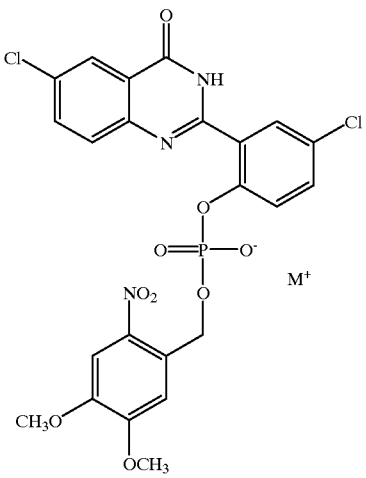

;

where M⁺ is a monovalent or divalent cation chosen from the group consisting of Na⁺, K⁺, NH₄⁺, Mg²⁺, and R₃NH⁺ where R is ethyl, methyl or isopropyl.

Other preferred compounds of the present invention include:

In the embodiments of Formula II:

  II both the enzymatically labile group and the caging group are attached to the luminescent functionality, rather than the caging group being attached to the enzymatically labile group. Preferred embodiments of the compounds of Formula II are those in which Z is chosen from the group consisting of

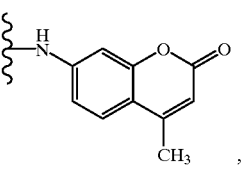,

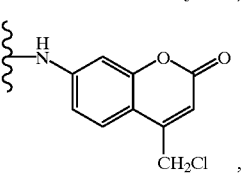,

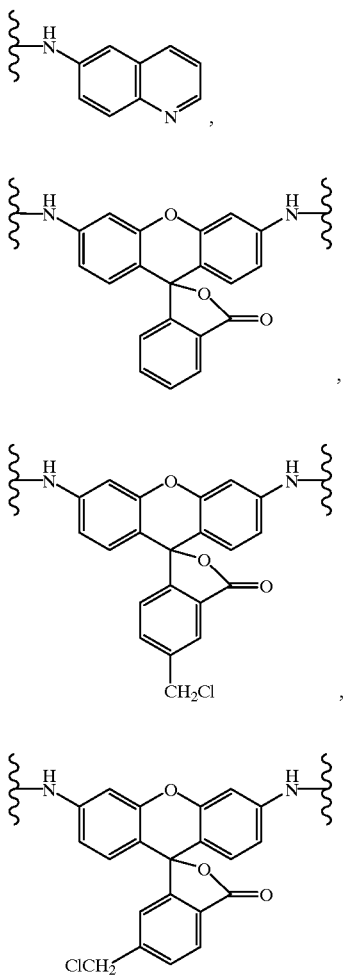

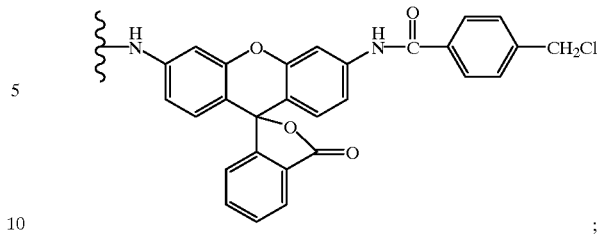

G is an amino acid, an N-terminally substituted amino acid, a side-chain-protected amino acid, a dipeptide, an N-terminally substituted dipeptide, a tripeptide or an N-terminally substituted tripeptide wherein the N-terminal functional group is chosen from the group consisting of acetyl, benzyloxy carbonyl or $R^2C(O)$— where $R^2$ is alkyl, alkoxy or aryloxy; and the amino acid or peptide is attached to the nitrogen of Z to form an amide; and K is chosen from the group consisting of 2-nitrobenzyl, 1-cyano-1-(2-nitrophenyl)methyl, 4,5-dimethoxy-2-nitrobenzyl, 2-nitrophenethyl, 4,5-dimethoxy-2-nitrophenethyl, phenacyl and substituted phenacyl.

Other preferred embodiments of the compounds of Formula II are those wherein G is an amino acid amide and K is chosen from the group consisting of 2-nitrobenzyl, 1-cyano-1-(2-nitrophenyl)methyl, 4,5-dimethoxy-2-nitrobenzyl, 2-nitrophenethyl, 4,5-dimethoxy-2-nitrophenethyl, phenacyl and substituted phenacyl.

Additional preferred compounds of the present invention include:

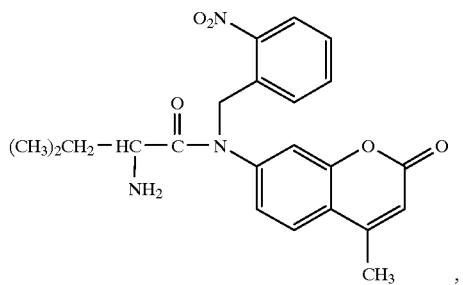

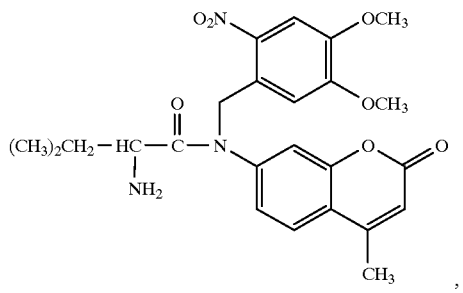

-continued

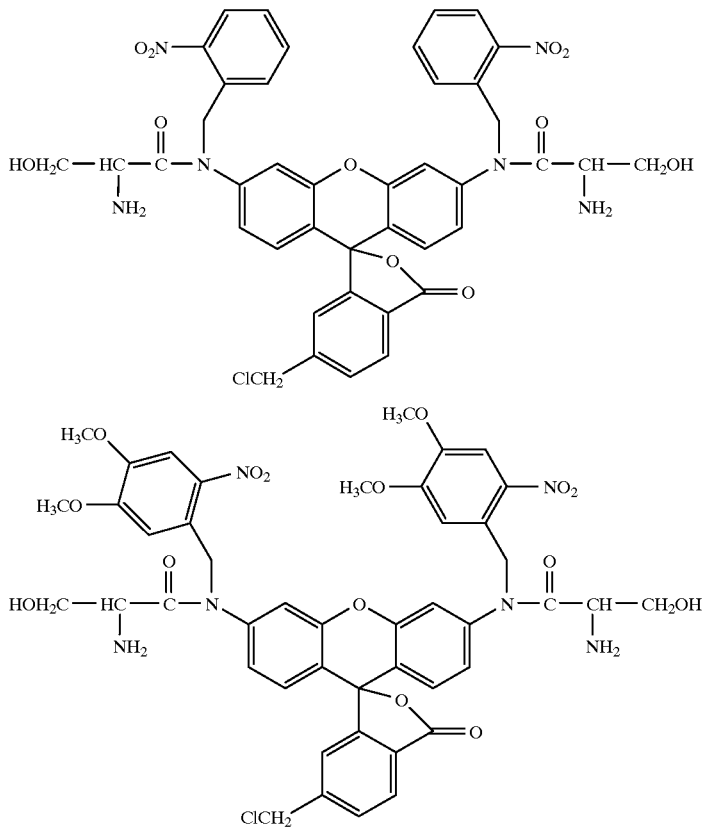

Examples of particular cages, represented as K in Formula I and Formula II include: 2-nitrobenzyl, 4,5-dimethoxy-2-nitrobenzyl and the like.

Another embodiment of the present invention is a method for determining reporter enzyme activity and, by inference, the activator or suppressor activity of test compounds in a cell-based assay. In the present invention, activator or suppressor activity of test compounds is determined by measuring the expression of a secreted reporter enzyme, which is proportional to a luminescent signal. A test compound can interact with one or more components of the signal transduction pathway connecting the receptor to the particular transcriptional and/or translational apparatus associated with a particular reporter gene to activate or suppress reporter enzyme expression. The points of interaction include (but are not restricted to): the ligand-binding domain of the receptor, the signaling domain of the receptor, the enzymes of the signal transduction and amplification cascade (which can include kinases, phosphatases, and other enzymes that post-translationally modify additional components of the pathway), nuclear pores, components of the transcriptional apparatus that cause gene transcription, mRNA modification and transport to the ribosome, ribosomal initiation and elongation factors. Functions associated with a specific localization or other processing of the disease-associated protein within the cell or the organism as a whole, are not mechanisms of action that are easily probed using the invention. Preferably, compounds of the present invention may be used in cell-based assays to determine reporter enzyme activity where the point of interaction is chosen from the group consisting of the ligand-binding domain, the signaling domain, the enzymes of the signal transduction and amplification cascade, nuclear pores and components of the transcriptional apparatus.

Cell-based assays for suppressor activity of test compounds require that reporter enzyme expression be activated through addition of an activator prior to addition of a test compound. Cells are activated at a particular time during incubation. Within twelve hours, the cage is released by a flash of light (<1 min). In a particularly preferred assay for suppressor activity, cell samples are placed in a device such as a Rayonet Photochemical Reactor which is capable of irradiating the cell samples with 8×4 W lamps (366 nm). Usual irradiation times are optimized between 10 sec to 1 min. Reporter enzyme activity, as seen by a luminescent signal, is measured after the cage is released. Within 30 sec to 1 min. after irradiation of the cell samples, the samples are positioned in a detector device such as a Victor 1420 Multilabel Scanner. The luminescent signal from each cell sample is measured for 1 sec–10 min and the signal is recorded in total counts. The resulting reporter enzyme expression decreases proportional to the suppressor activity demonstrated by a test compound.

Reporter gene assays for agonist activity of test compounds require that cells be incubated under conditions that facilitate expression of a reporter enzyme. A test compound can also be evaluated for activator activity. In this case, an increase in reporter enzyme expression relative to that associated with other test compounds is observed.

The method using the compounds of the present invention as caged substrates for determining reporter enzyme activity in a cell-based assay, preferably using cultured mammalian cells, is demonstrated by the scheme below. Note that no second addition of substrate is required.

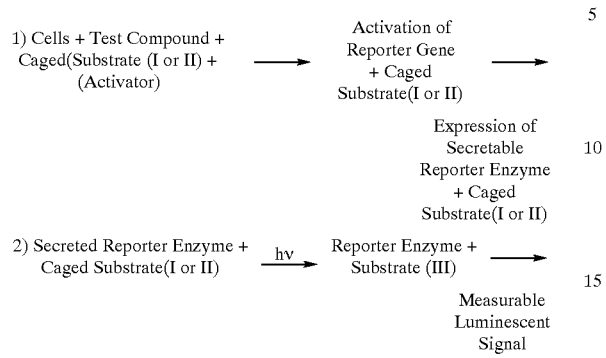

Mammalian cells are cultured under conditions that promote the expression of a secretable reporter enzyme. A caged substrate (Formula I or II), a test compound and, when applicable to assay for antagonist activity, an agonist, are present in the cell media. The reporter gene of interest is activated and expresses the secretable reporter enzyme. Irradiation of the assay mix cleaves the caging group by photolysis to release the enzyme substrate (Formula III). The reporter enzyme then cleaves the enzyme cleavable group, G, to release the luminescent functionality, Z. The luminescent functionality, Z, decomposes and releases energy as a luminescent signal. This signal measured is proportional to the reporter enzyme activity and therefore, represents the suppressor or activator activity of the test compound.

Agonists or stimulants commonly used in reporter enzyme assays include, but are not limited to: adenosine (A-016), dipyridamole (D-107), salbutamol (A-109), amoxapine (A-129), diazepam (D-120), FGIN I27 (F-129), bombesin (B-126), bradykinin (B-120), R(+)-methanandamine (M-186), cholecystokinin-8 (C-152), acetyl choline (A-112), hemicholinium-3 (H-108), cocaine (C-1 23), bFGF (B-148), propentofylline (P-205), dopamine (D-019), amantadine (A-132), endothelin-1 (E-134), L-glutamic acid (G-100), L-trans-pyrrolidine-2,4-dicarboxylic acid (P-167), baclofen (B-020), histamine (H-119), BU224 (B-154), galanin (G-219), oxytocin (O-117), neuropeptide Y (N-177), Leu-enkephalin (E-117), buspirone (B-119), clomipramine (C-129), Sp-8-[(4-chlorophenyl)thio]-cGMPS triethylamine (C-241), heparin sodium (H-153), arachidonic acid (A-203), PMA (P-145), and FK-888 (F-130). The numbers in parentheses refer to the Research Biochemicals International catalog (1997/1998) (1 Strathmore Road, Natick, Mass.). Additional agonists or stimulants include estrone (3-hydroxyestra-1,3,5(10)-trien-17-one), testosterone (17β-17-hydroxyandrost-4-en-3-one) and the like.

Antagonists or suppressors commonly used in reporter enzyme assays include, but are not limited to: alloxazine, lorglumide (L-109), HOE 140 (H-157), scopolamine (S-104), telenzepine (T-122), clozapine (C-171), reserpine (R-102), raclopride, quinpirole (Q-102), pirenzepine (P-114), terguride (T-165), lisuride (L 118), sulpiride (S-112), saclofen (S-166), 5-aminovaleric acid (A-120), and bicuculline (G-003).

A representative scheme for the caged substrates of this invention is shown in Scheme 2:

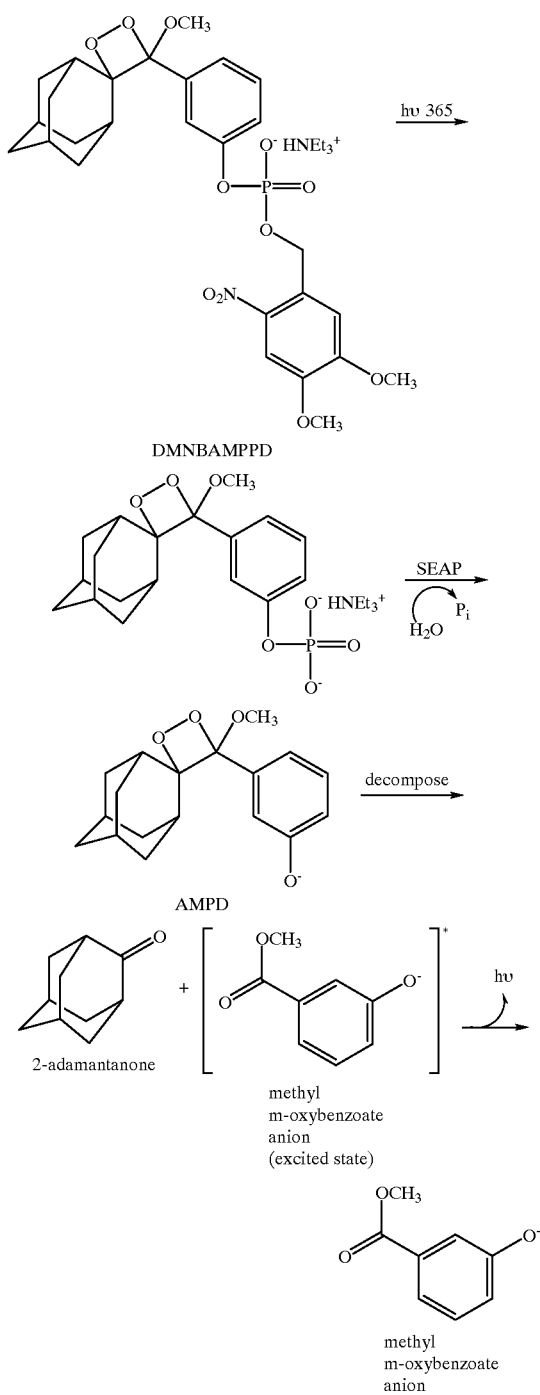

Photolytic cleavage of the 4,5-dimethoxy-2-nitrobenzyl caging group from DMNBAMPPD, present in the cell-based assay, generates the enzyme substrate AMPPD. SEAP cleaves the phosphate group to release the anion AMPD which decomposes to two carbonyl products, adamantone and the excited state aryl oxide anion. This aryl oxide anion releases energy as a luminescent signal. Detection of the luminescent signal provides a measurement of the reporter enzyme activity and thus, an indirect measurement of the activity of the particular test compound.

The assays described generally fall into the class of luminescence assays. In the context of the invention, luminescence is defined broadly to include both chemiluminescence and photoluminescence and photoluminescence includes both fluorescence and phosphorescence.

A one step addition of reagents in an assay for reporter enzyme activity is preferred. The reagents of the biological assay are added to microwell plates for determining the effects of test compounds on reporter enzyme activity. The microwell plate containing the cell sample and assay mixture is positioned in a device for delivering ultraviolet radiation. A preferred device is a Rayonet Photochemical Reactor fitted with 8×4 W UV lamps set to deliver 366 nm light. Examples of microwell plates used in the assay of test compounds include 96-microwell plates, 384-microwell plates and 1536-microwell plates. Therefore, this method is applicable to high throughput screening and assays in microwell plates. To release the enzyme substrate (Formula I or II), the microwell plate is irradiated with ultraviolet light to photolytically cleave the caging group. For preferred assays, 366 nm ultraviolet light is used and the duration of irradiation is 10 sec to 1 min.

Control of the UV light is maintained, for example, by a switch located on the Rayonet device which provides immediate UV irradiation of the sample or quick termination of UV light from the light source. Within 30 sec to 1 min. following release of the caging group, the microwell plate is positioned in a detector. A preferred detector is a Victor 1420 Multilabel Scanner which measures the luminescent signal from each microwell sample. The time period for measurement of the luminescent signal preferably is 1 sec–10 min and each signal is recorded as total counts. The length of time for recording the luminescent signal is determined empirically for the irradiation time period and the maximal level of reporter enzyme expression as seen by the intensity of the luminescent signal. Very intense signals are measured for a shorter duration and low intensity signals require longer periods for measurement of total counts, but each luminescent signal from each microwell sample is measured for the same duration of time within the same assay.

Comparison of luminescent signals from each microwell sample determines the relative influence of each test compound upon reporter enzyme activity. In assays for activators, increased reporter enzyme activity in the presence of a test compound is reflected by an increase in luminescent signal indicating that the test compound is an activator. For suppressor assays, high levels of reporter enzyme activity in the presence of a test compound and an activator indicates that the test compound is only a weak suppressor. The relative activity of a test compound may be compared against that of a known activator or suppressor in a cell-based assay. Additionally, the relative activity of a test compound may be ranked with the relative activities of other test compounds and compared to a control, e.g., the assay result when no test compound is present.

Luminescent signals are allowed to decrease for a period of time before more enzyme substrate is released. The usual time interval between measurements is five times $t_{1/2}$. For the preferred enzyme substrates of the present invention, such time interval is approximately 1 h. For the present invention, as described, $t_{1/2}$ is the elapsed time at which the observed signal reaches 50% of the value of the initial intensity. Sufficient time between measurement of luminescent signals is necessary to avoid high background signal and to decrease error in measurement.

Although general irradiation conditions, measurement conditions and cell growth conditions are disclosed, optimum conditions may be defined for each particular assay with no more than routine experimentation.

METHODS OF SYNTHESIS

The caged substrates of the present invention were prepared according to the following methods. Generally 0.1–0.5 g of each substrate is required for use in multiple biological assays. For actual synthesis, the appropriate reagents and reaction conditions were chosen to afford a desired quantity of caged enzyme substrate.

Preparation of Representative Tricyclo or Bicyclo Caged Enzyme Chemiluminescent Probes:

Scheme 3
General Preparation of Tricyclo or Bicyclo Caged Substrates

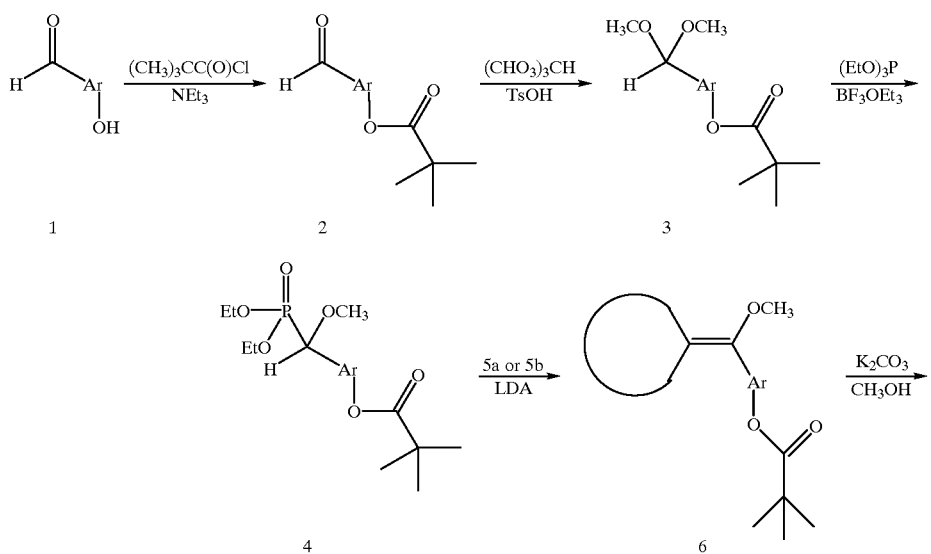

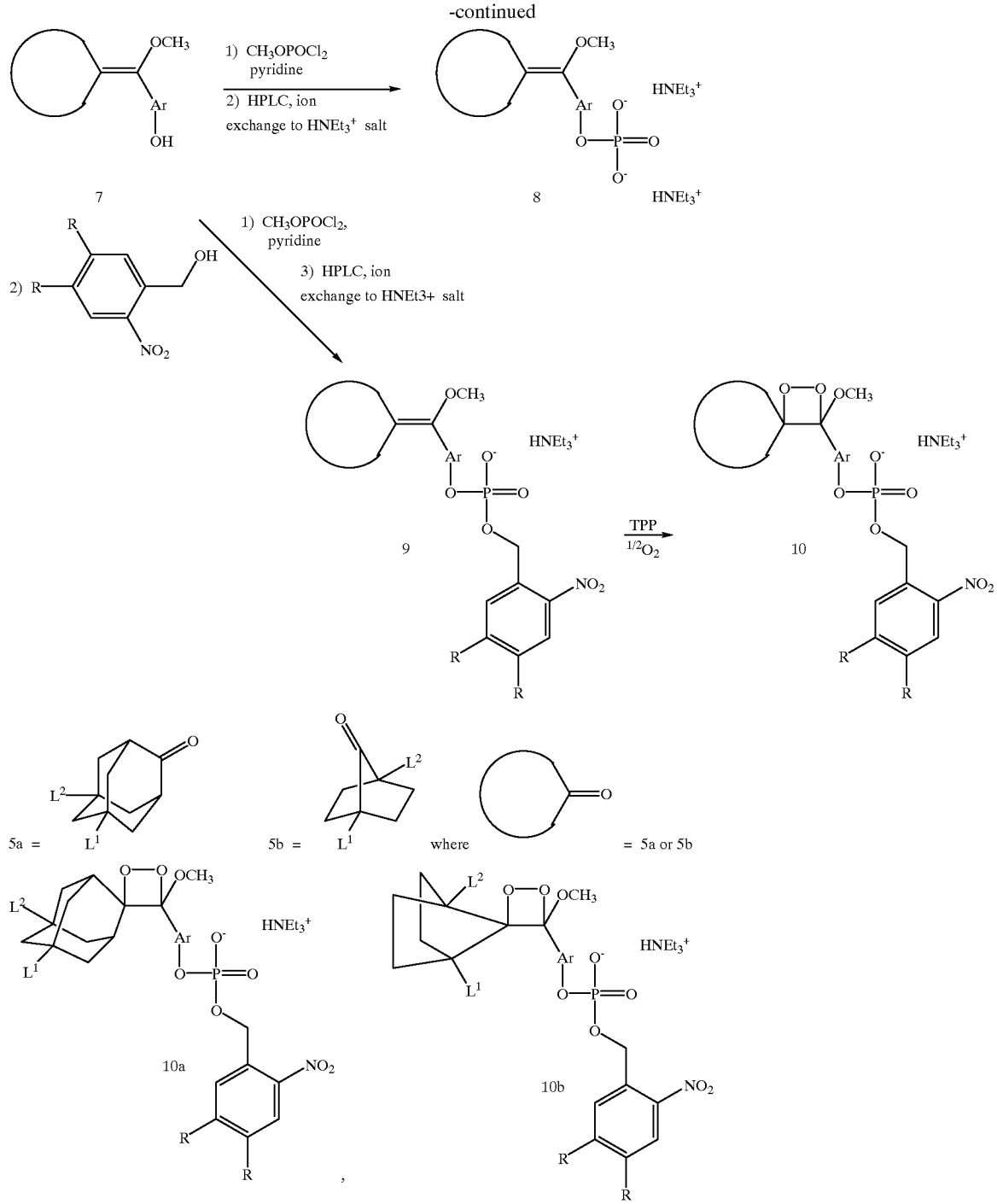

The alcohol 1 was treated with pivaloyl chloride and triethylamine to afford the ester aldehyde 2. Treatment of the ester aldehyde 2 with trimethyl orthoformate and p-toluenesulfonic acid afforded the dimethyl acetal 3. The dimethyl acetal 3 was treated with triethyl phosphite in boron trifluoride diethyl etherate to afford the diethyl phosphate ester 4. Coupling of the ester 4 with a bicyclo or tricyclo ketone 5 gave the tetra-substituted alkene aryl ester 6 which was hydrolyzed to afford aryl hydroxy compound 7 (U.S. Pat. No. 5,538,847, issued Jul. 23, 1996).

Conversion of the phenol 7 to the aryl phosphate 8 occurred under phosphorylation conditions with methyl dichlorophosphate in pyridine and subsequent treatment under aqueous conditions. Accordingly, treatment of the phenol 7 with methyl dichlorophosphate in pyridine followed by treatment with an appropriate 2-nitrobenzyl alcohol afforded the o-nitrobenzyl ester alkene 9 (Rubinstein, M., Patchornik, A., *Tetrahedron* 31, 2107–2110 (1975)). Formation of the desired dioxetane 10 resulted from treatment of the aryl phosphate 9 with 5, 10, 15, 20-tetraphenyl-21H, 23H-porphine (TPP) in chloroform and irradiation with a 250-W, high pressure sodium lamp at 10° C. under a stream of oxygen (Scheme 1) (Edwards, B., Sparks, A., Voyta, J. C., Strong, R., Murphy, O., Bronstein, I., *J. Org.*

Chem. 55, 6225–6229 (1990)). An alternative method involving the formation of the dioxetane using polymer-bound Rose Bengal bis (triethylammonium) salt with a 1000-W high pressure sodium lamp was also demonstrated (Schaap, P., Sandison, M., Handley, R. S., *Tetrahedron Letters* 28, 159–1162 (1987)).

Synthesis of Dioxetanes

R., Murphy, O., Bronstein, I., *J. Org. Chem.*, 55, 6225–6229 (1990) and (U.S. Pat. No. 5,538,847, issued Jul. 23, 1996)), was followed to prepare both the naphthalene and benzene derivatives (Scheme 4). Subsequent phosphorylation of 1-hydroxy-3-(methoxytricyclo[3.3.1.1$^{3,7}$]dec-2-ylidenemethyl)benzene with methyl dichlorophosphate in pyridine and coupling with 4,5-dimethoxy 2-nitrobenzyl

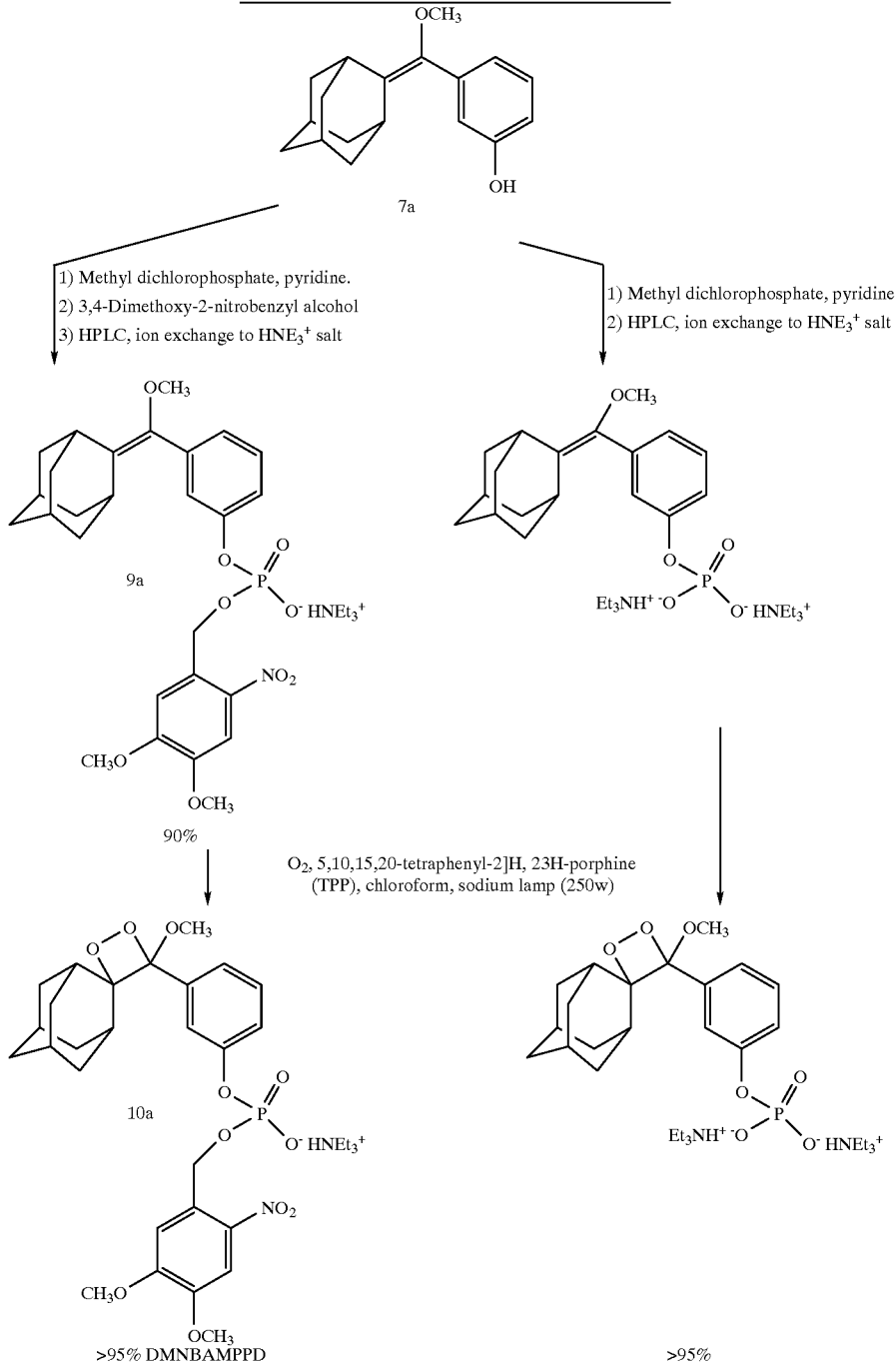

The procedure for the preparation of 6-hydroxy-2-(methoxytricyclo[3.3.1.1$^{3,7}$]dec-2-ylidene-methyl)naphthalene (Edwards, B., Sparks, A., Voyta, J. C., Strong, alcohol in pyridine (Rubinstein, M., Patchornik, A., *Tetrahedron* 31, 2107–2110 (1975)) afforded pyridinium 4,5-dimethoxy-2-nitrobenzyl 3-(methoxytricyclo[3.3.1.1$^{3,7}$]

dec-2-ylidenemethyl)phenyl phosphate, which, upon ion exchange to the triethylamine salt, provided compound 9a in Scheme 4. Oxidation afforded 4,5-dimethoxy-2-nitrobenzyl (4-methoxyspiro[1,2-dioxetane-3,2'-tricyclo[3.3.1.1$^{3,7}$] decan]-3-yl)phenyl phosphate as the triethylamine salt (compound 10a in Scheme 4) [see Edwards et al., *J. Org. Chem.*, 55, 6225–6229 (1990)]. Similarly, phosphorylation of 1-hydroxy-3-(methoxytricyclo[3.3.1.1$^{3,7}$]dec-2-ylidenemethyl)benzene with methyl dichlorophosphate in pyridine and coupling with 2-nitrobenzyl alcohol in pyridine followed by ion exchange to TEA salt and subsequent oxidation afforded triethylammonium 2-nitrobenzyl (4-methoxyspiro[1,2-dioxetane-3,2'-tricyclo[3.3.1.1$^{3,7}$] decan]-3-yl)phenyl phosphate.

Synthesis of Luminescent Amides

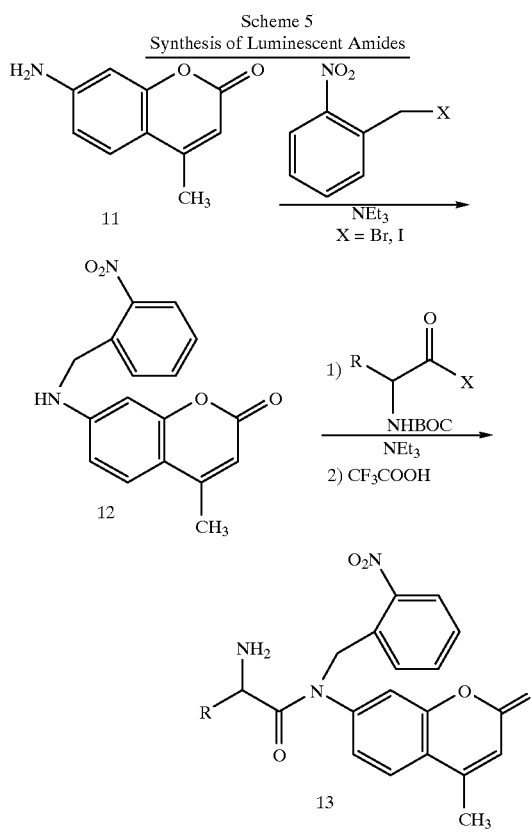

7-Amino-4-methylcoumarin 11 was treated with 2-nitrobenzyl halide in dimethylformamide in the presence of triethylamine to afford the corresponding secondary amine 12. The secondary amine 12 was treated with a BOC protected amino acyl halide in the presence of triethylamine followed by deprotection with trifluoroacetic acid to afford the amino acid amide 13 (Scheme 5).

Syntheses:
6-Hydroxy-2-(methoxytricyclo[3.3.1.1$^{3,7}$]dec-2-ylidenemethyl)naphthalene or benzene derivatives (7) were prepared by a reported procedure (Edwards, B., et al.,*J. Org. Chem.*, 55, 6225–6229 (1990)). Triethylammonium 3-(methoxytricyclo[3.3.1.1$^{3,7}$]dec-2-ylidenemethyl)phenyl phosphate: Methyl dichlorophosphate (0.1 mL, 1 mmol) was added dropwise to 5 mL of anhydrous pyridine at 0° C. The suspension was stirred at 0° C. for 15 min. The phenol 7 (11 mg. 0.04 mmol) in 0.5 mL pyridine was added dropwise. The suspension was stirred at rt for 40 min. At this point, the reaction was worked up to afford the phosphate 8. The solvent was removed under vacuum and the residue (0.3 g) was suspended in 1 mL acetonitrile. The separation of the phosphate was carried out by HPLC on a 250×10 mm C18 column with a gradient mixture of solvents 20 mM triethylammonium acetate pH 7 and acetonitrile. The purified phosphate 8 weighed 20 mg (91%). $^1$HNMR (CDCl$_3$): d 7.28 (t, 1 H, J=7.2), 7.15 (s, 1 H), 7.21 (d, 1 H, J=7.2), 6.79 (d, 1 H, J=7.2), 3.28 (s, 3 H), 3.22 (brs, 1 H), 2.98 (q, 4 H, J=7.2), 2.65 (brs, 1 H), 2.03–1.73 (m, 12 H), 1.24 (t, 6 H, J=7.2).

Triethylammonium 4,5-Dimethoxy-2-Nitrobenzyl 3-(methoxytricyclo[3.3.1.1$^{3,7}$]dec-2-ylidenemethyl)phenyl phosphate. Methyl dichlorophosphate (0.1 mL, 1 mmol) was added dropwise to 5 mL of anhydrous pyridine at 0° C. The suspension was stirred at 0° C. for 15 min. The phenol 7 (11 mg. 0.04 mmol) in 0.5 mL pyridine was added dropwise. The suspension was stirred at rt for 40 min, then a solution of 4,5-dimethoxy-2-nitrobenzyl alcohol (0. 213g, I mmol) in 1.5 mL pyridine was added. The suspension was stirred at rt for 4 h. Water (10 mL) was added and the solution was washed with ether (2×10 mL). The aqueous layer was extracted with chloroform (2×15 mL). The combined chloroform layers were dried (Na$_2$SO$_4$) and concentrated to gave 0.4 g of crude product as light yellow oil. HPLC purification as above gave 22 mg (93% yield) of 4,5-dimethoxy-2-nitrobenzyl caged phosphate 9a. $^1$H NMR d 7.70 (s, 1 H), 7.40 (s, 1 H), 7.33–7.14 (m, 3 H), 7.00(d, 1 H, J=7.5), 5.47 (d, 1 H, J=6.9), 3.93 (s, 3 H), 3.86 (s, 3 H), 3.23 (s, 3 H), 3.21 (brs, 1 H), 3.05 (q, 12 H, J=7.2), 2.60 (brs, 1 H), 2.06–1.67 (m, 12 H), 1.31 (t, 18H, J=7.2).

All other caged phosphates including caged 4-methylumbelliferyl phosphates were prepared by this procedure.

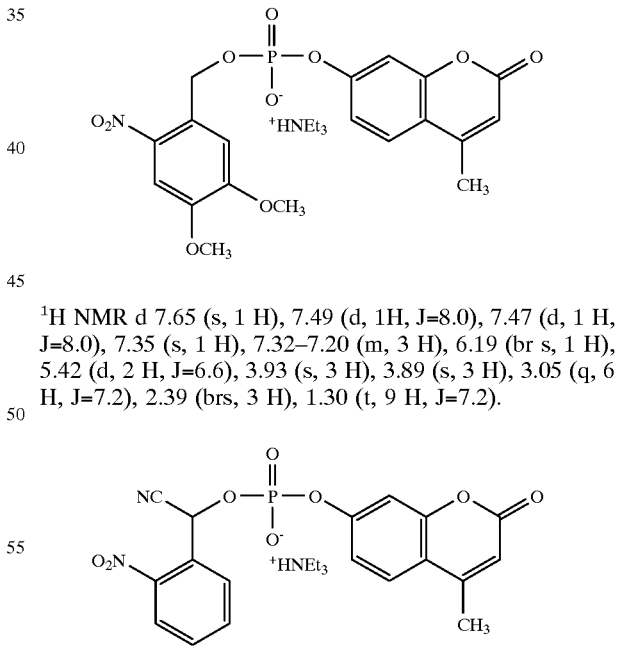

$^1$H NMR d 7.65 (s, 1 H), 7.49 (d, 1H, J=8.0), 7.47 (d, 1 H, J=8.0), 7.35 (s, 1 H), 7.32–7.20 (m, 3 H), 6.19 (br s, 1 H), 5.42 (d, 2 H, J=6.6), 3.93 (s, 3 H), 3.89 (s, 3 H), 3.05 (q, 6 H, J=7.2), 2.39 (brs, 3 H), 1.30 (t, 9 H, J=7.2).

$^1$H NMRd 8.12 (d, 1 H, J=7.4), 7.99 ((d, 1H, J=7.4), 7.68 (t, 1 H, J=7.4), 7.55 (t, 1 H, J=7.4), 7.43 (d, 1 H, J=7.6), 7.20 (d, 1 H, J=7.6), 7.09 (br s, 1 H), 6.72 (d, 1 H, J=9.2), 6.19 (br s, 1 H), 3.08 (q, 6 H, J=7.2), 2.39 (br s, 3 H), 1.30(t, 9 H, J=7.2).

Preparation of dioxetane phosphates 10a: Oxidation of the alkene was carried out by the reported procedure (Edwards, B., et al., *J. Org. Chem.*, 55, 6225–6229 (1990)), and monitored by 1H NMR and HPLC. The yields are >95%. $^1$H NMR d 7.69 (s, 1 H), 7.40 (s, 1 H), 7.39–7.20 (m, 4 H), 5.43 (d, 1 H, J=6.9), 3.93 (s, 3 H), 3.91 (s, 3 H), 3.16 (s, 3 H), 3.08 (q, 6 H, J=7.2), 300 (br s, 1 H), 2.06 (br s, 1 H), 1.82–1.50 (m, 10 H), 1.33 (t, 9 H, J=7.2), 1.13 (br d, 1 H, J=14), 0.95 (br d, 1 H, J=15).

The preparation of the NMPPD series was continued from the alkene 9b on a 0.1–0.5 g scale with stepwise yields of 80–99%.

NMR data for Norbornyl compounds

Pivalate 6b $^1$H NMR d 7.35 (t, 1 H, J=7.2), 7.25 (d, 1 H, J=7.2), 7.06 (br s, 1 H), 6.97 (d, 1 H, J=7.2), 3.43 (s, 3 H), 3.0 (br s, 1 H), 2.75 (br s, 1 H), 2.18 (br s, 2 H), 1.6–1.8 (m, 6 H), 1.2 (s, 9 H).

Phenol 7b $^1$H NMR d 7.2 (t, 1 H, J=7.2), 6.96(s, 1 H), 6.94 (t, 1 H, J=7.2), 6.8 (d, 1 H, J=7.2), 3.43 (s, 3 H), 3.0 (br s, 1 H), 2.73 (br s, 1 H), 2.18 (br s, 2 H), 1.6–1.8 (m, 6 H).

Caged phosphate 9b $^1$H NMR d 7.69 (s, 1 H), 7.39 (s, 1 H), 7.19–7.29 (m, 3 H), 7.04 (d, 1 H, J=7.2), 5.48 (d, 2 H, J=6.5), 3.90 (s, 3 H), 3.82 (s, 3 H), 3.39 (s, 3 H), 3.05 (q, 6 H, J,=7.2), 2.97 (br s, 1 H), 2.62 (br s, 1 H), 1.58–1.7 (m, 8 H), 1.30 (t, 9 H, J=7.2).

Caged NMPPD 10b $^1$HNMR d 7.70 (s, 1 H), 7.41 (s, 1 H), 7.19–7.42 (m, 4 H), 5.45 (d, 2 H, J=5.9), 3.90 (s, 3 H), 3.88 (s, 3 H), 3.22 (s, 3 H), 3.05 (q, 6 H, J,=7.2), 2.6 (br s, 1 H), 1.8 (br s, 1 H), 1.58–1.76 (m, 6 H), 1.35 (t, 9 H, J=7.2).1.06 (br d, 1 H, J=9), 0.85 (br d, J=9).

N-((N'-t-butoxycarbonyl)leucinyl) N-(2-nitrobenzyl)7-amido-4-methylcoumarin:

7-Amino-4-methylcoumarin 11 (3.12 mmol) is treated with 2-nitrobenzyl bromide (6.24 mmol) in TEA (6.26. mmol)/DMF (5 mL) to afford the secondary amine 12. Addition of t-butoxycarbonyl leucinyl chloride (prepared from t-butoxycarbonyl leucine and oxalyl chloride) (3.74 mmol) to the solution of 12 in DMF affords the title amide. Removal of the BOC protecting group is achieved using a solution of trifluoroacetic acid.

Compounds in which G is a sugar:

Glycosides can be prepared by methods well known to persons of skill in the art. See Hanessian, *Preparative Carbohydrate Chemistry*, Marcel Dekker, New York, 1997, the disclosure of which is incorporated herein by reference. For example, tetra-O-acetylglycopyranosyl halides or glycofuranosyl halides may be reacted with a metal salt of the appropriate luminescent phenol (e.g. 7-hydroxycoumarin). Hydrolysis of the 1-acetate, reaction with the appropriate benzyl halide (e.g. 2-nitrobenzyl bromide) and hydrolysis of the remaining three acetates provides the nitrobenzyl glycoside. In a similar manner, a caged substrate for galactosidase can be prepared from 1,2,3,4-di-O-isopropylidene-D-galactopyranose by (1) reaction with 2-nitrobenzyl bromide in the presence of sodium hydride; (2) hydrolysis of the isopropylidenes; (3) acetylation to the tetraacetate; (4) conversion of the 1-acetyl to bromide; (5) coupling of the bromide to the appropriate luminescent phenol (e.g. 7-hydroxycoumarin); and (6) hydrolysis of the remaining three acetates. These reactions are well known to persons of skill in the art.

Thio-D-glucosides and similar compounds can be prepared from glucose pentaacetate by reaction with the appropriate benzyl mercaptan (e.g. 2-nitrobenzyl mercaptan) in the presence of zinc chloride by the method of Wolfrom, followed by hydrolysis of the 1-acetate and Mitsunobu reaction with the appropriate luminescent phenol (e.g. 7-hydroxycoumarin). The remaining three acetates are then hydrolyzed. These reactions are also well known to persons of skill in the art.

Utility Of The Compounds Of The Invention

The compounds of the present invention are useful for detecting reporter enzyme activity in cell-based assays. Such cell-based assays include, but are not limited to, the following currently employed reporter genes:

Secreted alkaline phosphatase (SEAP), extracellular β-lactamase (Cartwright, C. P., Li, Y., Zhu, Y. S., Kang, Y. S. and Tipper, D. J., *Yeast* 10(4): 497–508 (1994)), intracellular β-lactamase (Zlokarnik, G., Negulescu, P. A., Knapp, T. E., Mere, L., Burres, N., Feng, L., Whitney, M., Roemer, K., and Tsien, R. Y., *Science* 279(5347): 84–88 (1998)), urokinase-plasminogen activator (Yokoyama-Kobayashi, M., Sugano, S., Kato, T. and Kato, S., *Gene* 163(2), 193–196 (1995), Zimmerman, M., Quigley, J. P., Ashe, B., Dorn, C., Goldfarb, R. Troll, W., *Proc. Natl. Acad. Sci. USA* 75, 750–753 (1978); Huseby, R. M., et al., *Thrombosis Research* 10, 679, (1977)), dipeptidyl peptidase IV (Beauvais, A., Monod, M., Wyniger, J., Debeaupuis, J. P., Grouzmann, E., Brakch, N., Svab, J., Hovanessian, A. G. and Latge, J. P., *Infection and Immunity* 65(8), 3042–3047 (1997)), butyrylcholinesterase (Blong, R. M., Bedows, E. and Lockridge, O., *Biochem. J.* 327(Pt 3), 747–757 (1997)), Renilla reniformis luciferase (Liu, J., O'Kane, D. J. and Escher, A., *Gene* 203(2), 141–148 (1997)), carbonic anhydrase VI (secreted) (Aldred, P., Fu, P., Barrett, G., Penschow, J. D., Wright, R., Coghlan, J. P., Fernley, R. T., *RL Biochemistry* 30, 569–575 (1991)), phospholipase A2 (Ramanadham, S., Ma, Z., Arita, H., Zhang, S. and Turk, J., *Biochim Biophys Acta* 1390 (3), 301–12 (1998)).

The benefits of using the compounds of the present invention for detection of reporter enzyme activity can be assessed using the assay systems specific to each reporter gene, as are well known in the art.

Materials for Cell-Based Assays 1536 microwell Corning plate—white tissue culture treated plate HEK293E-TK—Luc Cell line HEK293EBNA—purchased from Invitrogen (Carlsbad, Calif., cat. No. R620–07

Luciferase Assay System—Promega (Madison, Wis.)

Vasoactive-Intestinal Peptide (human, porcine, rat) Peninsula Labs, Ltd, Catalog #7161

Corning T75 Flask 15 ml conical tube

Media:

Dulbecco's Modified Eagle Media (D-MEM), High Glucose, with L-glutamine (Gibco Cat #11965–092).

0.5% Hygromycin B, liquid (Gibco #10687–010)

1% Penicillin-Streptomycin, liquid (Gibco #15140–031)

1% Glutamax-II Supplement (Gibco #25060–062)

10% Fetal Bovine Serum, Qualified (Gibco #26140–079)

Dulbecco's Phosphate Buffered Saline (Gibco #14040–133)

Hemacytometer

Stereomicroscope

EDTA (Ethylenediamine tetraacetic acid)

ddH$_2$O

Packard Luclite Assay Kit (#6016916) Packard Instruments, (Meriden, Conn.)

Hanks' Balanced Salt Solution (Gibco #14025–076)

Corning 245 mm sq. bioassay dish (#43 1111) Fisher

Blotting paper

PixSys dispenser Cartesian Tech., Inc. (Irvine, Calif.) Centrifuge

Incubator

Tundra Field Imager, Imaging Research, Inc. (St. Catharines, Ontario)

Rayonet photochemical reactor (Southern N.E. Ultraviolet Co., RMR-3500, Branford, Conn. 06805) (CAT# RMP3500)

Victor multilabel detector apparatus (Wallac OY PO Box 10, FIN-20101, Turku, Finland)

HEK-293 cells are particularly preferred and are available from the American Type Culture Collection (ATCC), Rockville, Md., Accession Number CRL-1573. HEK-293 cells that constitutively express EBNA1 are most preferred, and are commercially available from Invitrogen Corporation, Carlsbad, Calif. Other useful mammalian cell lines, particularly primate cell lines include: CV-1 African green monkey kidney cells, Jurkat cells, THP-1, any number of neuroblastoma or glioblastoma cells, and the like.

EXAMPLE

Biological Assay:

HEK293 mammalian cells do not produce alkaline phosphatase without a construct or a promoter. Thus, a typical assay using secreted placental alkaline phosphatase (SEAP) was designed by first assembling an artificial reporter gene construct wherein the expression of SEAP reporter gene in HEK293 cell line was induced by the elevation of the cyclic AMP (cAMP) levels by virtue of a genetic response element (CRE) and then, the concentration of SEAP released into the media was measured. The HEK293(CRE-SEAP) cell line thus constructed responds to VIP or VIP receptor agonists by increasing the level of SEAP expression. Detection of SEAP is somewhat improved because, since the cells are not destroyed by the measurement, the media can be replenished and the reporter activity can be measured subsequently.

For optimum efficiency in assessing the ability of compounds to activate or suppress specific cellular pathways that regulate secreted alkaline phosphatase (SEAP), a culture medium of cells was arrayed in a 96-well plate. The caged substrate (Scheme 4, Compound 10a) was added at a concentration of 10 to 100 $\mu$M. At any point during cell growth when measurement of the expression level of SEAP was desired, the o-nitrobenzyl cage was removed from the substrate by brief (1–10s) irradiation with long wavelength UV light (366 nm) (Scheme 2). Ideally, the irradiation occurred when the plate was situated for field imaging, e.g., on the stage of a CCD-camera-based optical imager like the SpeedReader available from SAIC (San Diego, Calif.). Photolysis during the described experiment was completed in RAYONET Photochemical Reactors (with 8×4 watts 366 nm lamps), available from Southern N.E. Ultraviolet Co., RMR-3500, Branford, Conn. 06805. Irradiation also can be provided by the illumination source of a field imager that is configured for both chemiluminescence and fluorescence measurements. For example, the SpeedReader uses a 1000 W Xe source lamp for fluorescence measurements, and this light source can be adjusted to emit light of the proper wavelength that provides cleavage energy for the photochemical release of substrate from the caged substrate.

Luminescence was measured with a Victor multilabel detector apparatus for the described experiment. To evaluate the stability of a representative caged enzyme substrate under cell-based incubation conditions, the caged enzyme substrate, DMNBAMPPD (10–100 $\mu$M) was incubated with HEK293 mammalian cells in a 96-microwell plate. After 12 h, alkaline phosphatase was added to some of the microwells. The microwell plate was irradiated for 1 min in the Rayonet photochemical reactor using 8×4 W UV lamps (366 nm) to release the enzyme substrate. The microwell plate containing the cell samples was positioned in a Victor 1420 Multilabel Scanner within 30 sec–1 min and luminescent signals were recorded for 1 second as total counts. Interaction of alkaline phosphatase and the uncaged enzyme substrate resulted in a measurable luminescent signal for microwells containing added alkaline phosphatase. Microwells without added alkaline phosphatase gave only a background luminescent signal. This experiment favorably evaluated the stability of the caged enzyme substrates of the present invention under typical cell growth conditions. The ability of the caged substrate to generate the enzyme substrate and detect alkaline phosphatase through measurable luminescence was also demonstrated.

After removal of the caging group by irradiation, the uncaged chemiluminescent substrate is dephosphorylated to afford the aryloxy anion which decomposes to release energy as light (FIG. 3). The total light released from each well is directly related to the length of irradiation, but the time course of light emission under certain conditions is directly related to the level of SEAP present in the cell, as illustrated by the following equations:

$$S \sim C \xrightarrow{k_{irr}} S, \text{ where: } k_{irr} \propto \Phi I \tag{1}$$

$$S \xrightarrow{k_{app}} P*, \text{ where: } k_{app} = \frac{k_{cat}[E]}{K_m + [S]} \tag{2}$$

$$P* \xrightarrow{k_{decomp}} P + h\nu \tag{3}$$

where S~C is the caged substrate 1, S is the uncaged substrate released by photolysis, P* is the product of the phosphatase reaction, and P is the decomposition product of P* after chemiluminescent decomposition. As described by these equations, the amount of light emitted in a given length of time is sensitive to the concentration of SEAP, [E], when $k_{app} << k_{irr}$, $k_{decomp}$. In the equations, $\Phi$ is the quantum efficiency and I is the intensity of the incident light, [E] is the concentration of SEAP, and [S] is the ambient concentration of substrate. The apparent rate constant for photodecomposition of S~C, $k_{irr}$, can in principle be arbitrarily large with sufficient intensity of the illuminating light source. The Michaelis constant $K_m$ and catalytic turnover rate $k_{cat}$ describe in simple terms the rate of turnover of substrate into product by an enzyme. The $K_m$ for the substrate is generally much larger than the [S], such that the apparent rate constant $k_{app}$ is$(k_{cat}/K_m)[E]$ for the phosphatase reaction, but even if this condition is not valid, the rate of the production of P* is directly proportional to the concentration of SEAP (i.e., [E]). The rate constant for decomposition of the phosphatase product P*, $k_{decomp}$, is fixed by the chemistry of the substrate.

Thus, to compare the expression levels directly, the light emitted from the sample is measured for a defined period of time (1 s to 30 min). The time period for measurement of the chemiluminescent signal is determined empirically for the irradiation time and maximal expression level of SEAP in the absence of a candidate suppressor (when the suppression of gene induction is sought) or from the irradiation time and background level of the assay in the absence of a candidate activator (when the activation of gene expression is sought). Typically, the measurement time period is determined under the precise experimental conditions of the screen. Since many factors can influence the intensity of the light in the sample and therefore affect the kinetics and intensity of the resulting chemiluminescent signal, controlled experimental conditions are necessary to insure accurate assay results. Measurement of the released light over a defined period of time is an important aspect affecting experimental conditions. The total amount of light released will be defined by the total amount of substrate released, and will, in theory, be constant for all wells.

To measure the SEAP concentration at different time intervals during a total time period for continued cell incubation, the process is repeated. Sufficient time between irradiations must be allowed for the decay of the initial signal. Since the concentration of enzyme will influence the intensity of the light that is released, at least five half-lives (with the crucial measurement here being the least intense well in which a valid, repeat measurement is desired) must elapse before beginning the photocycle again. This rest time will allow each well to darken prior to the next irradiation and measurement of signal. Practically, this will limit consecutive measurements of SEAP to a rate of approximately one per hour. This general assay can identify the activity of a compound as an activator and/or suppressor and determine the relative level of activity.

Specific Biology Assays Using SEAP as a Reporter Gene:

HEK293 cells derived from human embryonic kidneys (Graham, F. L., *J. Gen. Virol.* 36, 59–72 (1977)) are known to express endogenous type I vasoactive intestinal peptide (VIP) receptors. Stimulation of the vasoactive intestinal peptide (VIP) receptor in the human embryonic kidney cell line HEK293 may be performed by constructing a reporter gene chimera wherein the expression of SEAP is induced by the elevation of the cyclic AMP (cAMP) levels by virtue of a genetic response element (CRE) positioned at the 5'-end of the gene. Stimulation of the VIP receptor is known to cause elevation of the cAMP levels, and consequently, the HEK293(CRE-SEAP) cell line thus constructed responds to VIP or VIP receptor agonists by increasing the level of SEAP expression.

To monitor the expression of SEAP over time in this system, the caged substrate DMNBAMPPD is added to a culture of HEK293(CRE-SEAP) and a VIP agonist (either a test compound or VIP itself) is added to the same culture. At the time a measurement of SEAP concentration is desired, the sample is illuminated for 1 min to release the cage from DMNBAMPPD, the illumination is extinguished, and the light that is emitted from the SEAP-catalyzed decomposition of AMPPD (the uncaged product of DMNBAMPPD) is collected and quantitated over 10 min. The amount of light released in this period of time correlates to the expression level of SEAP, and hence to the degree of stimulation of the CRE genetic element.

Another example involving stimulation of the estrogen receptor in the human liver carcinoma cell line HepG2 is performed by constructing a reporter gene chimera wherein the expression of SEAP is induced by the activation of estrogen-responsive pathways by virtue of a genetic response element (ERE) positioned at the 5'-end of the gene. Stimulation of the estrogen receptor is known to stimulate genes fused to the ERE element, and consequently, the HepG2(ERE-SEAP) cell line thus constructed responds to estrogen or estrogen receptor agonists by increasing the level of SEAP expression. To monitor the expression of SEAP over time in this system, the caged substrate DMN-BAMPPD is added to a culture of HepG2(ERE-SEAP) and an estrogen agonist (either a test compound or estrogen itself) is added to the same culture. At the time a measurement of SEAP concentration is desired, the sample is illuminated for 10 sec to release the cage from DMNBAMPPD, the illumination is extinguished, and the light that is emitted from the SEAP-catalyzed decomposition of AMPPD (the uncaged product of DMNBAMPPD) is collected and quantitated over 10 min. The amount of light released in this period of time correlates to the expression level of SEAP, and hence to the degree of stimulation of the ERE genetic element.

Another example involves stimulation of the insulin receptor in Chinese hamster ovary (CHO) cells expressing high levels of the insulin receptor (CHO-IR). The assay is performed by constructing a reporter gene chimera wherein the expression of SEAP is induced by the activation of insulin-responsive pathways by virtue of a genetic response element (the serum response element, SRE, derived from the c-fos promoter) positioned at the 5'-end of the gene. Stimulation of the insulin receptor is known to stimulate genes fused to the SRE element, and consequently, the CHO-IR (SRE-SEAP) cell line thus constructed responds to insulin or insulin receptor agonists by increasing the level of SEAP expression. To monitor the expression of SEAP over time in this system, the caged substrate DMNBAMPPD is added to a culture of CHO-IR(SRE-SEAP) and an insulin agonist (either a test compound or insulin itself) is added to the same culture. At the time a measurement of SEAP concentration is desired, the sample is illuminated for 1 min to release the cage from DMNBAMPPD, the illumination is extinguished, and the light that is emitted from the SEAP-catalyzed decomposition of AMPPD (the uncaged product of DMNBAMPPD) is collected and quantitated over 10 min. The amount of light released in this period of time correlates to the expression level of SEAP, and hence to the degree of stimulation of the SRE genetic element.

General Preparation of Assay Mixture

To assay for SEAP using the caged substrates of the present invention, the caged enzyme substrate is incorporated into the cell growth media and the cage is progressively released at certain intervals throughout the assay period to allow multiple readings. For example, DMNBAMPPD (FIG. 2) is incorporated into the media as the substrate prior to cell stimulation and growth. Cells are grown in bulk, giving $10^2$–$10^3$ cells per microliter in tissue culture media containing 10–100 $\mu$M DMNBAMPPD. This suspension is placed, in 1 $\mu$L aliquots, into each microwell of a 1536-microwell tissue culture treated polystyrene plate, available from Corning Life Sciences Products Division (Acton, Mass.). After 1.5 hr of incubation at 37° C., 5% $CO_2$, in a tissue-culture chamber ("Cell Culture Chamber For Multiple Well Plates", U.S. patent application Ser. No. 09/055,850, Filed Apr. 6, 1998), the microwell plate is removed and test samples (0.5 $\mu$L) are added to each well of the plate ("Methods And Apparatus For High Throughput Plate Or Plate To Membrane Transfer", U.S. patent application Ser. No. 09/055,855, Filed Apr. 6, 1998). After 12 h incubation at 37° C., 5% $CO_2$ the microwell plate is removed and irradiated (1 min). The light produced by the sample is quantitated in a field imager such as the Tundra from Imaging Research (St. Catharines, Ontario). Thus, cells that respond by producing SEAP in the media produce an amount of light (collected over 10 min) that is proportional to the concentration of SEAP in the media.

The described caged enzyme substrates can be used as probes for reporter gene activity in cell-based assays wherein an enzyme capable of cleaving the substrate is produced. Release of the enzyme substrate from the cage allows interaction of the enzyme substrate with the expressed reporter enzyme to provide a luminescent signal. Conventional assay formats are well known to those of skill in the art. A disclosure of suitable assays appears in U.S. Pat. No. 5,665,543, issued Sep. 9, 1997, incorporated herein by reference. It should be understood, however, that the assay format, per se, does not constitute an aspect of the present invention.

While the present invention has been described with reference to the specific embodiments thereof, it should be understood by those skilled in the art that various changes may be made and equivalents substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A caged substrate for reporter gene assays, comprising a compound of Formula I:

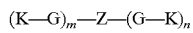

wherein:
- Z is a luminescent functionality;
- G is a labile group, cleavable by enzymatic action; and
- K is a photolytically cleavable caging group;
- wherein m and n are independently 0 or 1, but m and n both can not be zero.

2. The caged substrate of claim 1 wherein:
Z is chosen from the group consisting of

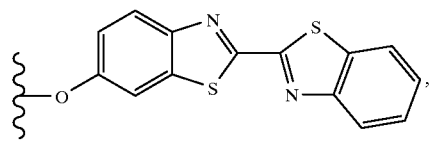

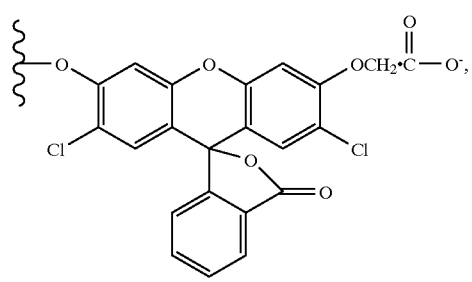

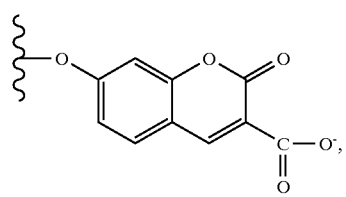

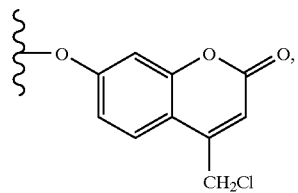

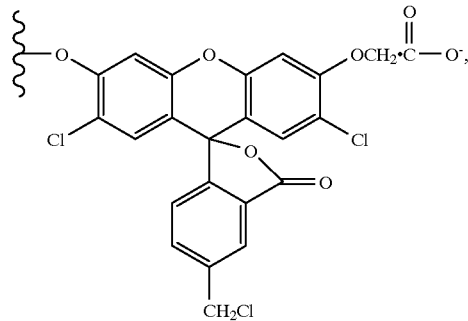

-continued

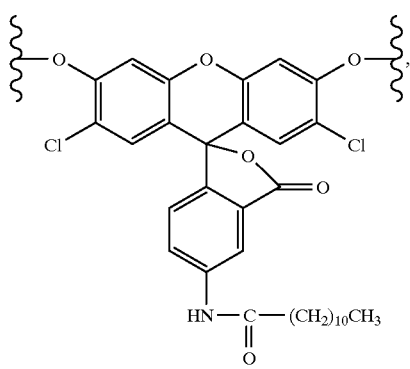

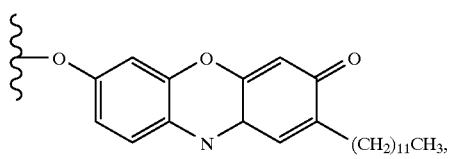

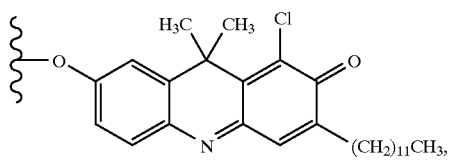

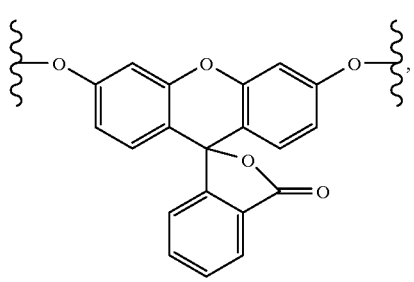

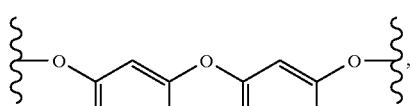

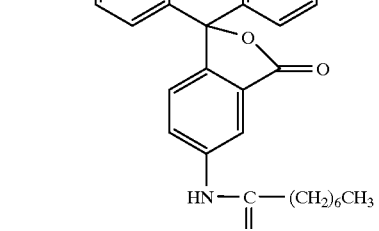

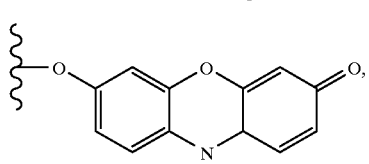

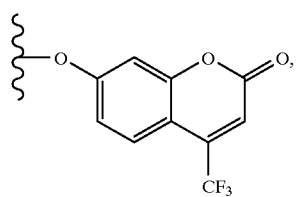

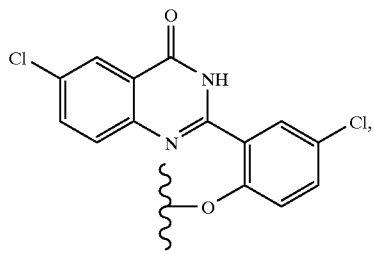

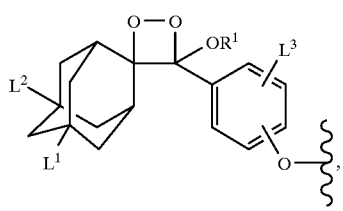

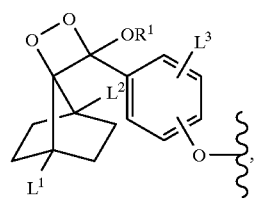

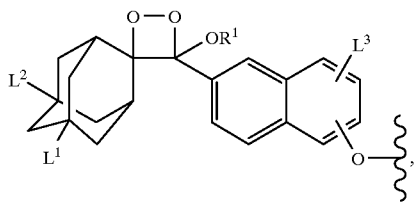

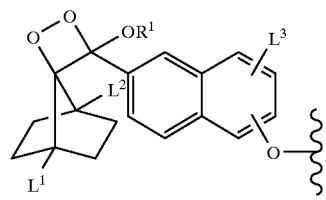

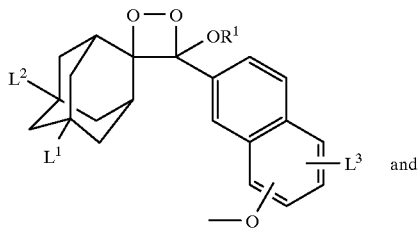 and

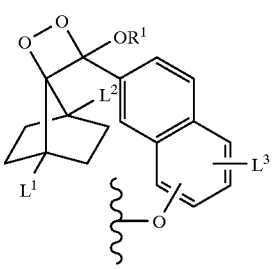

wherein $R^1$ is chosen from the group consisting of $C_{1-20}$ alkyl, substituted alkyl, aryl, substituted aryl, aralkyl and substituted aralkyl;

$L^1$, $L^2$ and $L^3$ are independently alkoxy, alkoxy phenoxy, amide, carboxyl, cyano, halogen, hydrogen, hydroxy, hydroxy alkoxy, phenyl, substituted phenyl or unsubstituted lower alkyl;

G is chosen from the group consisting of phosphate, galactoside, sulfonate, 1-phospho-2,3-diacylglyceride, 1-thio-D-glucoside, adenosine, α-D-glucoside, β-D-glucoside, β-D-glucuronide, β-D-mannoside, β-D-fructofuranoside, and β-glucosiduronate; and K is chosen from the group consisting of substituted benzyl, substituted benzylidene, phenacyl, substituted phenacyl, substituted phenethyl and 1-benzoylbenzyl.

3. The caged substrate of claim 2 wherein:

G is phosphate; and

K is chosen from the group consisting of 2-nitrobenzyl, 1-cyano-1-(2-nitrophenyl)methyl, 4,5-dimethoxy-2-nitrobenzyl, 2-nitrophenethyl, 4,5-dimethoxy-2-nitrophenethyl, phenacyl and substituted phenacyl.

4. The caged substrate of claim 3 of the formula chosen from the group consisting of

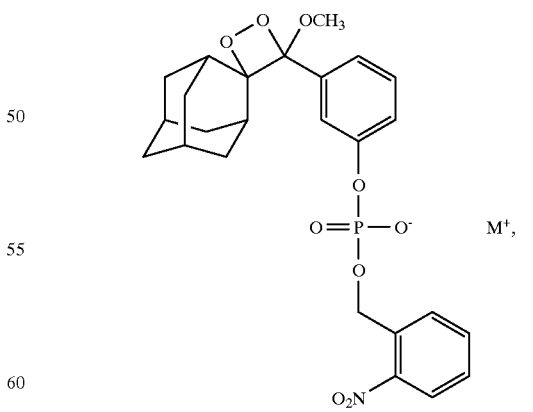

-continued
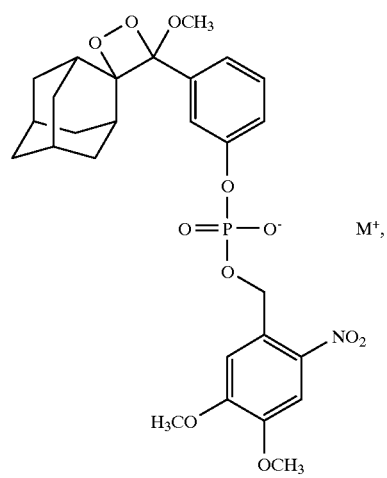
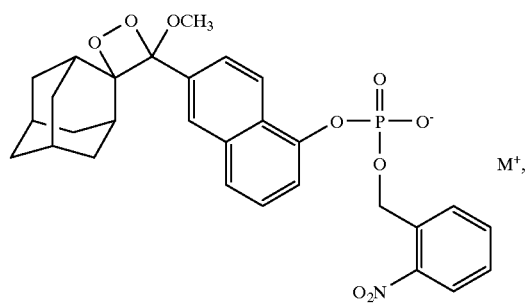
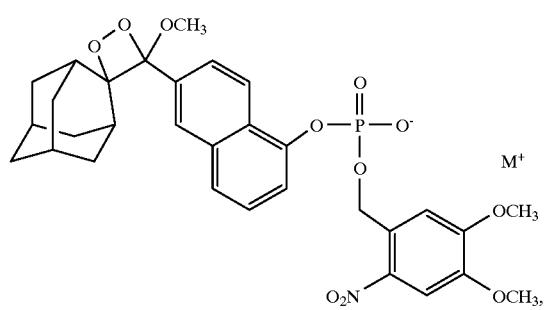
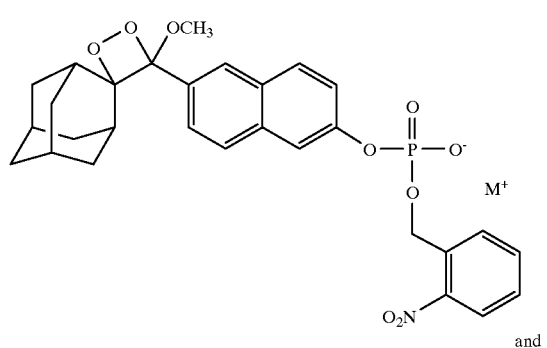
-continued
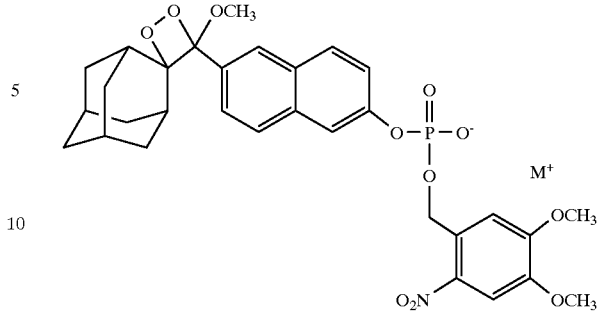
where M⁺ is a monovalent or divalent cation chosen from the group consisting of $Na^+$, $K^+$, $NH_4^+$, $Mg^{2+}$, and $R_3NH^+$ where R is ethyl, methyl or isopropyl.
5. The caged substrate of claim 3 of the formula:
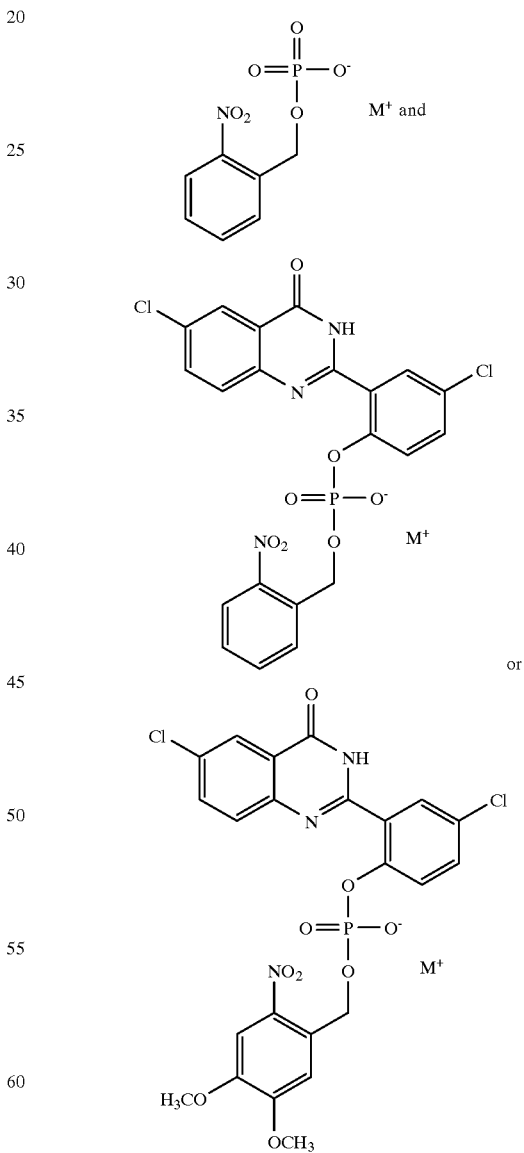

where M⁺ is a monovalent or divalent cation chosen from the group consisting of Na⁺, K⁺, NH₄⁺, Mg²⁺, and R₃NH⁺ where R is ethyl, methyl or isopropyl.

6. The caged substrate of claim 2 wherein:
   R₁ is C₁₋₄ alkyl.

7. The caged substrate of claim 2 wherein:
   L¹, L² and L³ are independently hydrogen, alkoxy, amide, carboxy or halogen.

8. A caged substrate for reporter gene assays, comprising a compound of Formula II:

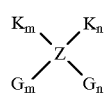

wherein:
   Z is a luminescent functionality;
   G is a labile group, cleavable by enzymatic action; and
   K is a photolytically cleavable caging group;
   wherein m and n are independently 0 or 1, but m and n both can not be zero.

9. The caged substrate of claim 8 wherein:
   Z is chosen from the group consisting of

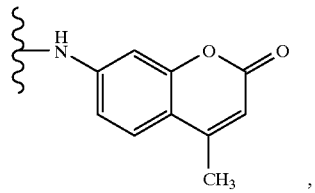

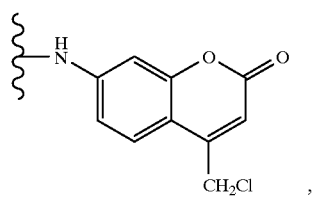

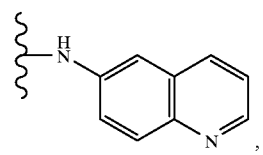

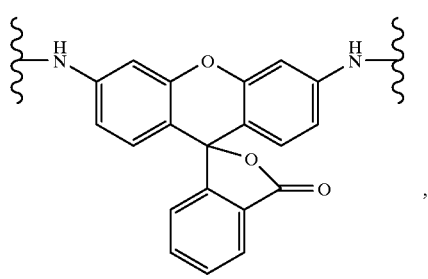

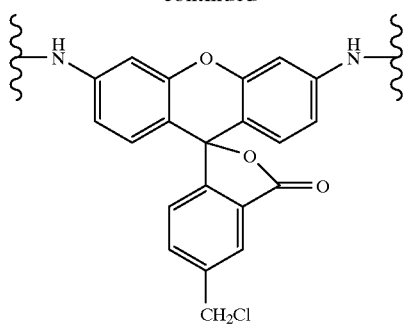

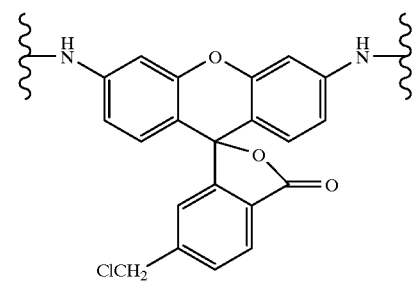

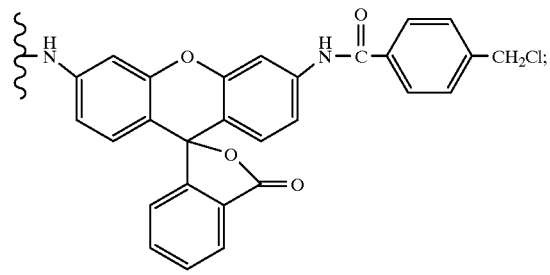

G is an amino acid, an N-terminally substituted amino acid, a side-chain-protected amino acid, a dipeptide, an N-terminally substituted dipeptide, a tripeptide or an N-terminally substituted tripeptide wherein the N-terminal functional group is chosen from the group consisting of acetyl, benzyloxy carbonyl or R²C(O)— where R² is alkyl, alkoxy or aryloxy; and the amino acid or peptide is attached to the nitrogen of Z to form an amide; and K is chosen from the group consisting of substituted benzyl, substituted benzylidene, phenacyl, substituted phenacyl, substituted phenethyl and 1-benzoylbenzyl.

10. The caged substrate of claim 9 wherein:
    G is an amino acid; and
    K is chosen from the group consisting of 2-nitrobenzyl, 1-cyano-1-(2-nitrophenyl)methyl, 4,5-dimethoxy-2-nitrobenzyl, 2-nitrophenethyl, 4,5-dimethoxy-2-nitrophenethyl, phenacyl and substituted phenacyl.

11. The caged substrate of claim 8 of the formula chosen from the group consisting of

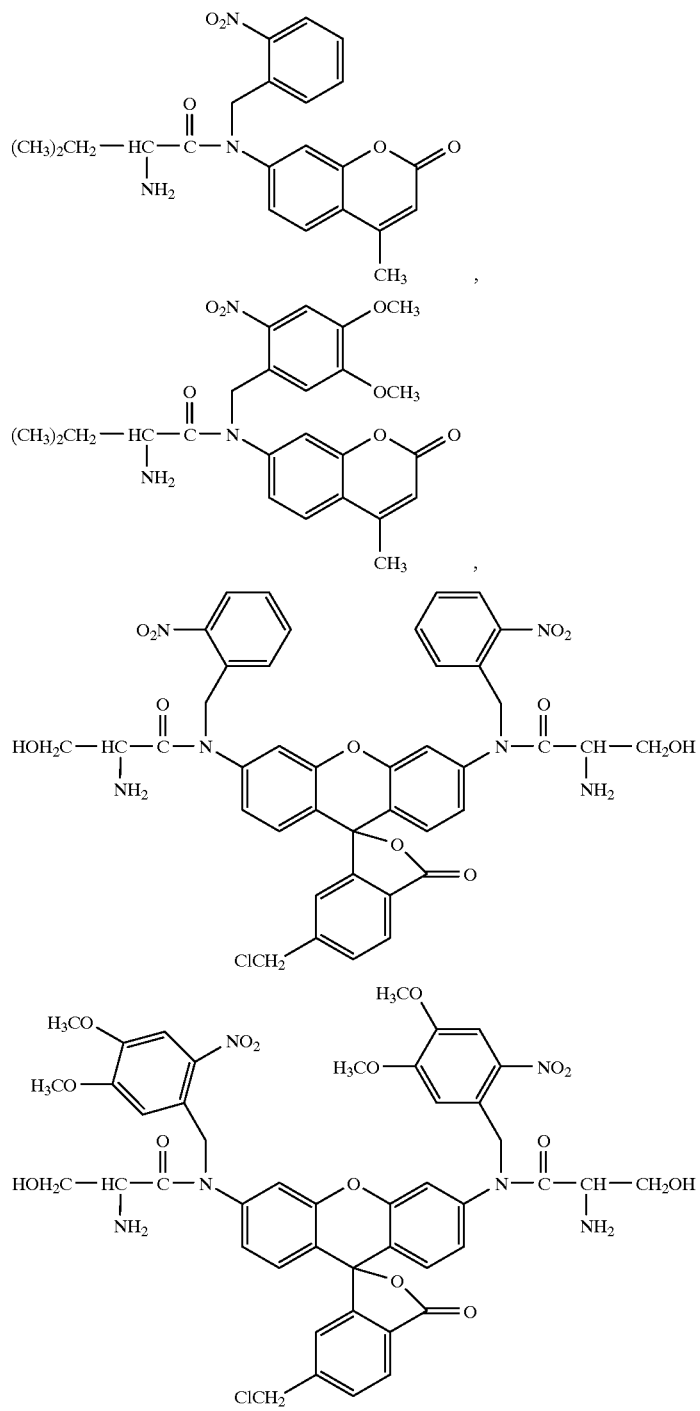

12. A test kit for determining reporter enzyme activity in a cell-based assay, comprising a compound of Formula I:

wherein:

Z is a luminescent functionality;
G is a labile group, cleavable by enzymatic action; and
K is a photolytically cleavable caging group;

wherein m and n are independently 0 or 1, but m and n both can not be zero;

wherein photolytic cleavage of moieties K produces a compound of Formula III:

13. A method for determining reporter enzyme activity in a cell-based assay comprising the steps of:

a) adding the compound of Formula I:

to a cell sample wherein:

Z is a luminescent functionality;

G is a labile group, cleavable by enzymatic action; and

K is a photolytically cleavable caging group;

wherein m and n are independently 0 or 1, but m and n both can not be zero;

b) contacting said cell sample with a test compound;

c) growing said cell sample such that a reporter gene enzyme is expressed;

d) controlling irradiation of the cell sample containing said compound of Formula I to photolytically cleave K and produce a compound of Formula III:

$$G_m\text{—}Z\text{—}G_n \qquad \text{III}$$

e) allowing said reporter gene enzyme to react with said compound of Formula III to enzymatically cleave G and produce a compound, Z, capable of producing a luminescent signal;

f) measuring the luminescent signal; and g) correlating said signal to the activity of said test compound.

14. A test kit for determining reporter enzyme activity in a cell-based assay, comprising a compound of Formula II:

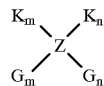

wherein:

Z is a luminescent functionality;

G is a labile group, cleavable by enzymatic action; and

K is a photolytically cleavable caging group;

wherein m and n are independently 0 or 1, but m and n both can not be zero;

wherein photolytic cleavage of moieties K produces a compound of Formula III:

$$G_m\text{—}Z\text{—}G_n. \qquad \text{III}$$

15. A method for determining reporter enzyme activity in a cell-based assay comprising the steps of:

a) adding the compound of Formula II:

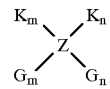

to a cell sample wherein:

Z is a luminescent functionality;

G is a labile group, cleavable by enzymatic action; and

K is a photolytically cleavable caging group;

wherein m and n are independently 0 or 1, but m and n both can not be zero;

b) contacting said cell sample with a test compound;

c) growing said cell sample such that a reporter gene enzyme is expressed;

d) controlling irradiation of the cell sample containing said compound of Formula II to photolytically cleave K and produce a compound of Formula III:

$$G_m\text{—}Z\text{—}G_n; \qquad \text{III}$$

e) allowing said reporter gene enzyme to react with said compound of Formula III to enzymatically cleave G and produce a compound, Z, capable of producing a luminescent signal;

f) measuring the luminescent signal; and g) correlating said signal to the activity of said test compound.

16. The method of claim 13 wherein said activity of the test compound is agonist activity.

17. The method of claim 15 wherein said activity of the test compound is agonist activity.

18. The method of claim 13 wherein said activity of the test compound is antagonist activity.

19. The method of claim 15 wherein said activity of the test compound is antagonist activity.

* * * * *